(12) United States Patent
Erlander et al.

(10) Patent No.: US 9,447,470 B2
(45) Date of Patent: Sep. 20, 2016

(54) TUMOR GRADING AND CANCER PROGNOSIS

(75) Inventors: Mark G. Erlander, Camino del Prado, CA (US); Xiao-Jun Ma, San Diego, CA (US); Dennis C. Sgroi, Winchester, MA (US)

(73) Assignees: bioTheranostics, Inc., San Diego, CA (US); The General Hospital Corporation, Boston, MA (US)

( * ) Notice: Subject to any disclaimer, the term of this patent is extended or adjusted under 35 U.S.C. 154(b) by 0 days.

(21) Appl. No.: 12/718,973

(22) Filed: Mar. 6, 2010

(65) Prior Publication Data

US 2011/0136680 A1   Jun. 9, 2011

Related U.S. Application Data

(63) Continuation-in-part of application No. PCT/US2008/075528, filed on Sep. 6, 2008.

(60) Provisional application No. 60/970,529, filed on Sep. 6, 2007.

(51) Int. Cl.
*C12Q 1/68* (2006.01)

(52) U.S. Cl.
CPC ....... *C12Q 1/6886* (2013.01); *C12Q 2600/106* (2013.01); *C12Q 2600/112* (2013.01)

(58) Field of Classification Search
None
See application file for complete search history.

(56) References Cited

U.S. PATENT DOCUMENTS

2005/0079518 A1   4/2005   Baker et al.

FOREIGN PATENT DOCUMENTS

| WO | WO 2005/008213    | 1/2005  |
|----|-------------------|---------|
| WO | WO 2005/079518    | 4/2005  |
| WO | WO 2006/119593 A1 | 11/2006 |
| WO | WO 2006/132971 A2 | 12/2006 |

OTHER PUBLICATIONS

Gonzalez-Angulo et al., Future of Personalized Medicine in Oncology: A Systems Biology Approach; Journal of Clinical Oncology, vol. 28, No. 16, pp. 2777-2783, 2010.*
Paik, Molecular profiling of breast cancer; Breast Cancer, vol. 18, pp. 59-63, 2006.*
Sotiriou et al., Gene Expression Profiling in Breast Cancer: Understanding the Molecular Basis of Histologic Grade to Improve Prognosis; Journal of the National Cancer Institute, vol. 98, No. 4, pp. 262-272, 2006.*
Lewis et al., Molecular Classification of Melanoma Using Real-Time Quantitative Reverse Transcriptase-Polymerase Chain Reaction; Cancer, vol. 104, No. 8, 00. 1678-1686, 2005.*
de Vos et al., Gene Expression Profile of Serial Samples of Transformed B-Cell Lymphomas; Laboratory Investigation, vol. 83, No. 2. p. 271-285, 2003.*
Lu et al., Selection of Potential Markers for Epithelial Ovarian Cancer with Gene Expression Arrays and Recursive Descent Partition Analysis; Clinical Cancer Research, vol. 10, pp. 3291-3300, 2004.*
Bepler et al. RRM1 and PTEN As Prognostic Parameters for Overall and Disease-Free Survival in Patients With Non-Small-Cell Lung Cancer; vol. 22, No. 10, p. 1878-1885, 2004.*
Collins et al., The application of genomic and proteomic technologies in predictive, preventive and personalized medicine; Vascular Pharmacology, vol. 45, pp. 258-267, 2006.*
Abramovitz and Leyland-Jones, a systems approach to clinical oncology: Focus on breast cancer; Proteome Science, vol. 4, No. 5, 2006.*
Romond et al., Trastuzumab plus Adjuvant Chemotherapy for Operable HER2-Positive Breast Cancer; New England Journal of Medicine, vol. 353, No. 16, pp. 1673-1684, 2005.*
Gianni et al., Feasibility and Tolerability of Sequential Doxorubicin/Paclitaxel Followed by Cyclophosphamide, Methotrexate, and Fluorouracil and Its Effects on Tumor Response as Preoperative Therapy; Clinical Cancer Research, vol. 11, No. 24, pp. 8715-8721, 2005.*
Ansfield et al., Ten-Year Study of 5-Fluorouracil in Disseminated Breast Cancer with Clinical Results and Survival Times; Cancer Research, vol. 29, pp. 1062-1066, 1969.*
Ma et al., A two-gene expression ratio predicts clinical outcome in breast cancer patients treated with tamoxifen; Cancer Cell, vol. 5, pp. 607-616, 2004.*
Cornfield et al., The Prognostic Significance of Multiple Morphologic Features and Biologic Markers in Ductal Carcinoma in Situ of the Breast; Cancer, vol. 100, No. 11, pp. 2317-2327, 2004.*
Soteriou et al., Gene Expression Profiling in Breast Cancer: Understanding the Molecular Basis of Histologic Grade to Improve Prognosis; Journal of the National Cancer Institute, vol. 98, No. 4, suplemental data, 2006.*
Yuan et al., Increase expression of mitotic checkpoint genes in breast cancer cells with chromosomal instability; Human Cancer Biology, vol. 12, No. 2, pp. 405-410, 2006.*

(Continued)

*Primary Examiner* — Addison D Ault
(74) *Attorney, Agent, or Firm* — Jones Day

(57) ABSTRACT

The disclosure includes the identification and use of gene expression profiles, or patterns, with clinical relevance to cancer. In particular, the disclosure includes the identities of genes that are expressed in correlation with tumor grade. The levels of gene expression are disclosed as a molecular index for determining tumor grade in a patient and predicting clinical outcome, and so prognosis, for the patient. The molecular grading of cancer may optionally be used in combination with a second molecular index for diagnosing cancer and its prognosis. The disclosure further includes methods for predicting cancer recurrence, and/or predicting occurrence of metastatic cancer. For diagnosis or prognosis, the disclosure further includes methods for determining or selecting the treatment of cancer based upon the likelihood of life expectancy, cancer recurrence, and/or cancer metastasis.

9 Claims, 11 Drawing Sheets

(56) References Cited

OTHER PUBLICATIONS

Dalgin et al., Portraits of breast cancer progression; BMC Bioinformatics, vol. 8, No. 291, pp. 1-16, Aug. 2007.*
Ester et al., Proceedings of the American Association for Cancer Research Annual Meeting, 46:1052 (Apr. 2005).
Chng and Fonesca, Blood, 108:967A (Nov. 2006).
Yamamoto et al., Cancer Genetics and Cytogenetics, 174:42-47 (Mar. 27, 2007).
Scintu et al., Cancer Letters, 254:298-308 (2007).

* cited by examiner

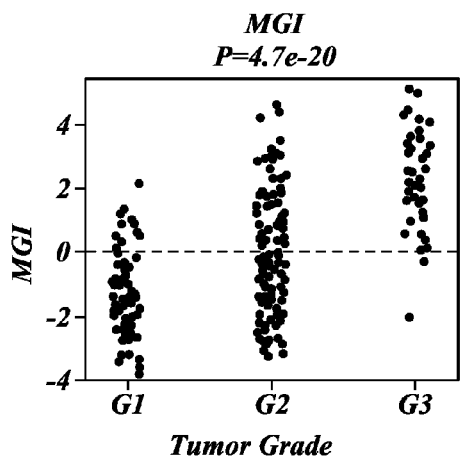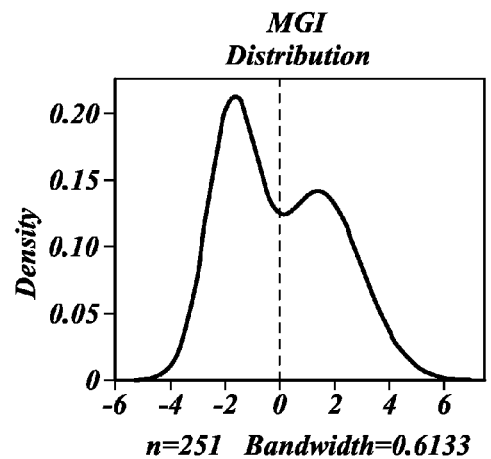
FIG.1A
FIG.1B
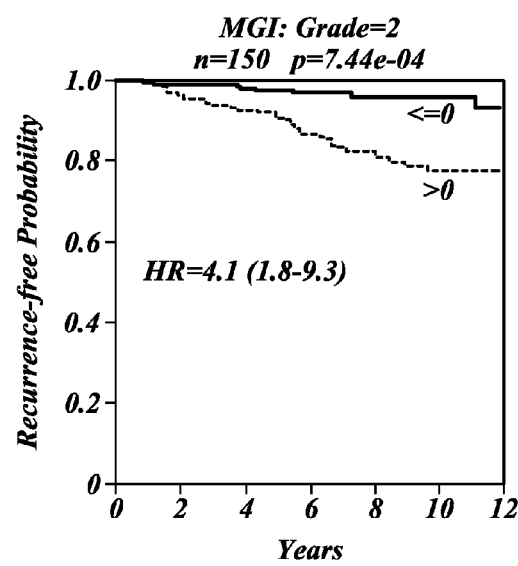
FIG.1C

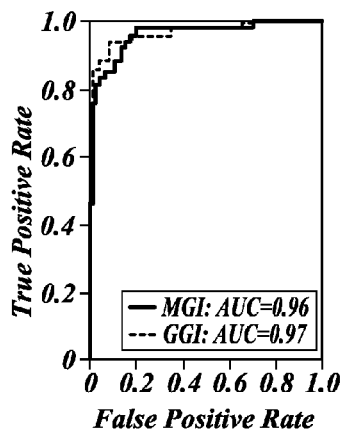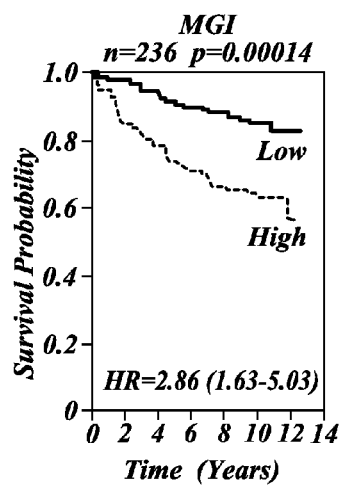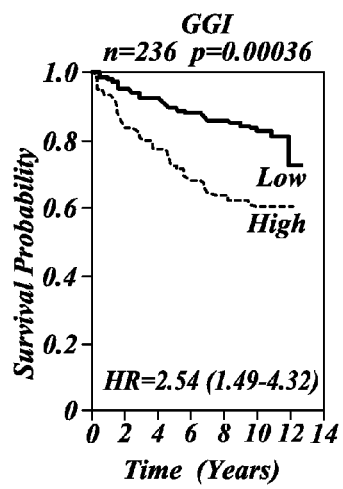
FIG.2A  FIG.2B  FIG.2C
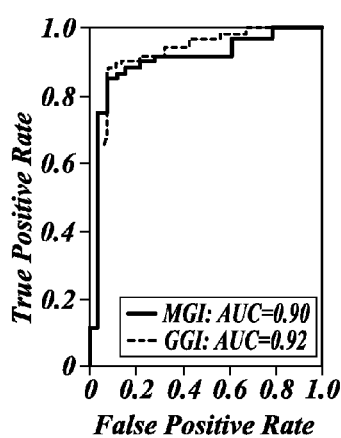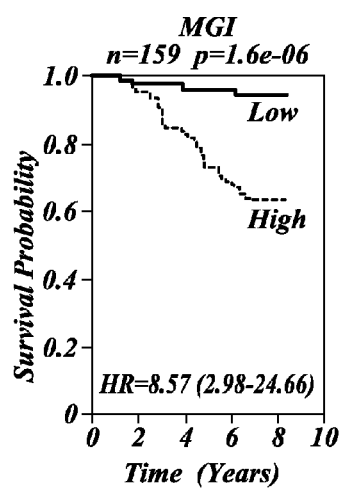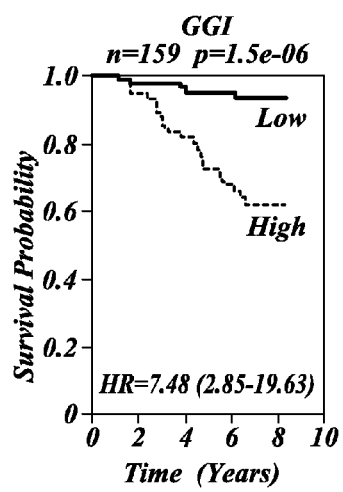
FIG.2D  FIG.2E  FIG.2F

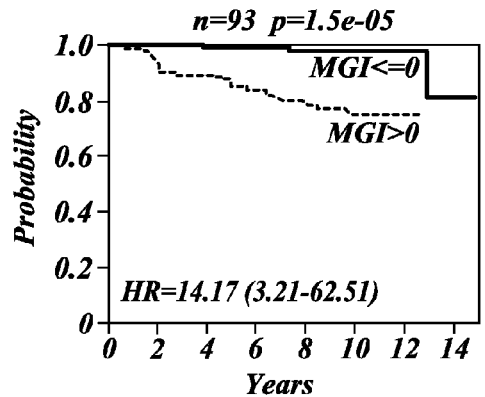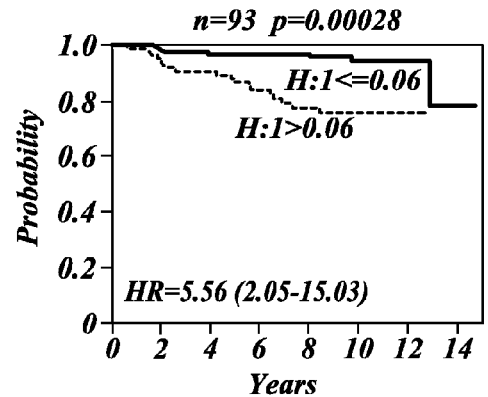
FIG.5A    FIG.5B
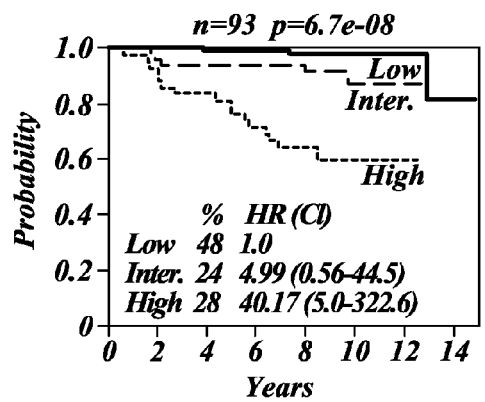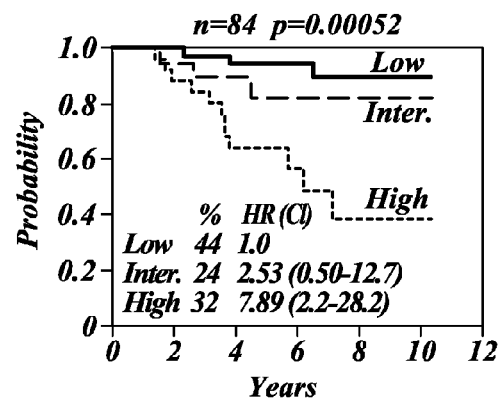
FIG.5C    FIG.5D

SEQUENCE LISTING

<160> NUMBER OF SEQ ID NOS: 25

<210> SEQ ID NO 1
<211> LENGTH: 21
<212> TYPE: DNA
<213> ORGANISM: Artificial Sequence
<220> FEATURE:
<223> OTHER INFORMATION: PCR Primer

<400> SEQUENCE: 1
gcctcagagc aatggttgta t          21

<210> SEQ ID NO 2
<211> LENGTH: 17
<212> TYPE: DNA
<213> ORGANISM: Artificial Sequence
<220> FEATURE:
<223> OTHER INFORMATION: Probe sequence

<400> SEQUENCE: 2
actgtatgtg ctgtaat              17

<210> SEQ ID NO 3

```
<211> LENGTH: 26
<212> TYPE: DNA
<213> ORGANISM: Artificial Sequence
<220> FEATURE:
<223> OTHER INFORMATION: PCR Primer

<400> SEQUENCE: 3
tagtgcatct aaatgtgtcc taaatt                                              26

<210> SEQ ID NO 4
<211> LENGTH: 22
<212> TYPE: DNA
<213> ORGANISM: Artificial Sequence
<220> FEATURE:
<223> OTHER INFORMATION: PCR Primer

<400> SEQUENCE: 4
gtgcttgtca acggatgtgt ag                                                  22

<210> SEQ ID NO 5
<211> LENGTH: 17
<212> TYPE: DNA
<213> ORGANISM: Artificial Sequence
<220> FEATURE:
<223> OTHER INFORMATION: Probe sequence

<400> SEQUENCE: 5
tcagaaactt aattggg                                                        17

<210> SEQ ID NO 6
<211> LENGTH: 27
<212> TYPE: DNA
<213> ORGANISM: Artificial Sequence
<220> FEATURE:
<223> OTHER INFORMATION: PCR Primer

<400> SEQUENCE: 6
catcaaagct tacaggtttt ctattca                                             27

<210> SEQ ID NO 7
<211> LENGTH: 19
<212> TYPE: DNA
<213> ORGANISM: Artificial Sequence
<220> FEATURE:
<223> OTHER INFORMATION: PCR Primer

<400> SEQUENCE: 7
cccatgagcc atgcctttc                                                      19

<210> SEQ ID NO 8
<211> LENGTH: 18
<212> TYPE: DNA
<213> ORGANISM: Artificial Sequence
<220> FEATURE:
<223> OTHER INFORMATION: Probe sequence

<400> SEQUENCE: 8
agtacacatg atatttcg                                                       18

<210> SEQ ID NO 9
<211> LENGTH: 26
<212> TYPE: DNA
<213> ORGANISM: Artificial Sequence
<220> FEATURE:
<223> OTHER INFORMATION: PCR Primer

<400> SEQUENCE: 9
```
gttgctgaag aacagtaaaa ccaatt                                              26

<210> SEQ ID NO 10
<211> LENGTH: 24
<212> TYPE: DNA
<213> ORGANISM: Artificial Sequence
<220> FEATURE:
<223> OTHER INFORMATION: PCR Primer

<400> SEQUENCE: 10
ggcatcccaa ctaacaataa agag                                               24

<210> SEQ ID NO 11
<211> LENGTH: 20
<212> TYPE: DNA
<213> ORGANISM: Artificial Sequence
<220> FEATURE:
<223> OTHER INFORMATION: Probe sequence

<400> SEQUENCE: 11
tataagggaa gattgtcaat                                                    20

<210> SEQ ID NO 12
<211> LENGTH: 26
<212> TYPE: DNA
<213> ORGANISM: Artificial Sequence
<220> FEATURE:
<223> OTHER INFORMATION: PCR Primer

<400> SEQUENCE: 12
atgactgtag cttttcttac cacaaa                                             26

<210> SEQ ID NO 13
<211> LENGTH: 22
<212> TYPE: DNA
<213> ORGANISM: Artificial sequence
<220> FEATURE:
<223> OTHER INFORMATION: PCR primer

<400> SEQUENCE: 13
cctttaacca gcacagccag tt                                                 22

<210> SEQ ID NO 14
<211> LENGTH: 15
<212> TYPE: DNA
<213> ORGANISM: Artificial Sequence
<220> FEATURE:
<223> OTHER INFORMATION: Probe sequence

<400> SEQUENCE: 14
aaagatgcag cctca                                                         15

<210> SEQ ID NO 15
<211> LENGTH: 22
<212> TYPE: DNA
<213> ORGANISM: Artificial sequence
<220> FEATURE:
<223> OTHER INFORMATION: PCR primer

<400> SEQUENCE: 15
cattaaaatc tgcgttgaag ca                                                 22

<210> SEQ ID NO 16
<211> LENGTH: 3649
<212> TYPE: DNA

<213> ORGANISM: Artificial Sequence
<220> FEATURE:
<223> OTHER INFORMATION: Bub 1B mRNA sequences

<400> SEQUENCE: 16

```
ggtcgcttct gtagctccga gggcaggttg cggaagaaag cccaggcggt ctgtggccca    60
gaggaaaggc ctgcagcagg acgaggacct gagccaggaa tgcaggatgg cggcggtgaa   120
gaaggaaggg ggtgctctga gtgaagccat gtccctggag ggagatgaat gggaactgag   180
taaagaaaat gtacaacctt taaggcaagg gcggatcatg tccacgcttc agggagcact   240
ggcacaagaa tctgcctgta acaatactct tcagcagcag aaacgggcat ttgaatatga   300
aattcgattt tacactggaa atgaccctct ggatgtttgg gataggtata tcagctggac   360
agagcagaac tatcctcaag gtgggaagga gagtaatatg tcaacgttat tagaaagagc   420
tgtagaagca ctacaaggag aaaaacgata ttatagtgat cctcgatttc tcaatctctg   480
gcttaaatta gggcgtttat gcaatgagcc tttggatatg tacagttact tgcacaacca   540
agggattggt gtttcacttg ctcagttcta tatctcatgg gcagaagaat atgaagctag   600
agaaaacttt aggaaagcag atgcgatatt tcaggaaggg attcaacaga aggctgaacc   660
actagaaaga ctacagtccc agcaccgaca attccaagct cgagtgtctc ggcaaactct   720
gttggcactt gagaagaag aagaggagga agttttgag tcttctgtac cacaacgaag   780
cacactagct gaactaaaga gcaaagggaa aaagacagca agagctccaa tcatccgtgt   840
aggaggtgct ctcaaggctc aagccagaa cagaggactc caaaatccat ttcctcaaca   900
gatgcaaaat aatagtagaa ttactgtttt tgatgaaaat gctgatgagg cttctacagc   960
agagttgtct aagcctacag tccagccatg gatagcaccc ccatgccca gggccaaaga  1020
gaatgagctg caagcaggcc cttgaacac aggcaggtcc ttggaacaca ggcctcgtgg  1080
caatacagct tcactgatag ctgtacccgc tgtgcttccc agtttcactc catatgtgga  1140
agagactgca aacagccag ttatgacacc atgtaaaatt gaacctagta taaaccacat  1200
cctaagcacc agaaagcctg gaaaggaaga aggagatcct ctacaaaggg ttcagagcca  1260
tcagcaagcg tctgaggaga agaaagagaa gatgatgtat tgtaaggaga agatttatgc  1320
aggagtaggg gaattctcct ttgaagaaat tcgggctgaa gttttccgga gaaaattaaa  1380
agagcaaagg gaagccgagc tattgaccag tgcagaagag agcagaaa tgcagaaaca  1440
gattgaagag atggagaaga agctaaaga aatccaaact actcagcaag aaagaacagg  1500
tgatcagcaa gaagagacga tgcctacaaa ggagacaact aaactgcaaa ttgcttccga  1560
gtctcagaaa ataccaggaa tgactctatc cagttctgtt tgtcaagtaa actgttgtgc  1620
cagagaaact tcacttgcgg agaacatttg gcaggaacaa cctcattcta aggtcccag   1680
tgtacctttc tccattttg atgagtttct tctttcagaa aagaagaata aaagtcctcc   1740
tgcagatccc ccacgagttt tagctcaacg aagaccccct tgcagttctca aaacctcaga   1800
aagcatcacc tcaaatgaag atgtgtctcc agatgtttgt gatgaattta caggaattga   1860
accctttgagc gaggatgcca ttatcacagg cttcagaaat gtaacaattt gtcctaaccc   1920
agaagacact tgtgacttg ccagagcagc tcgttttgta tccactcctt ttcatgagat   1980
aatgtccttg aaggatctcc cttctgatcc tgagagactg ttaccggaag aagatctaga   2040
tgtaaagacc tctgaggacc agcagacagc ttgtggcact atctacagtc agactctcag   2100
catcaagaag ctgagcccaa ttattgaaga cagtcgtgaa gccacacact cctctggctt   2160
ctctggttct tctgcctcgg ttgcaagcac ctcctccatc aaatgtcttc aaattcctga   2220
```

```
gaaactagaa cttactaatg agacttcaga aaaccctact cagtcaccat ggtgttcaca    2280
gtatcgcaga cagctactga agtccctacc agagttaagt gcctctgcag agttgtgtat    2340
agaagacaga ccaatgccta agttggaaat tgagaaggaa attgaattag gtaatgagga    2400
ttactgcatt aaacgagaat acctaatatg tgaagattac aagttattct gggtggcgcc    2460
aagaaactct gcagaattaa cagtaataaa ggtatcttct caacctgtcc catgggactt    2520
ttatatcaac ctcaagttaa aggaacgttt aaatgaagat tttgatcatt tttgcagctg    2580
ttatcaatat caagatggct gtattgtttg gcaccaatat ataaactgct tcacccttca    2640
ggatcttctc caacacagtg aatatattac ccatgaaata acagtgttga ttatttataa    2700
ccttttgaca atagtggaga tgctacacaa agcagaaata gtccatggtg acttgagtcc    2760
aaggtgtctg attctcagaa acagaatcca cgatccctat gattgtaaca agaacaatca    2820
agctttgaag atagtggact tttcctacag tgttgacctt agggtgcagc tggatgtttt    2880
taccctcagc ggctttcgga ctgtacagat cctggaagga caaagatcc tggctaactg    2940 ttcttctccc taccaggtag acctgtttgg tatagcagat ttagcacatt tactattgtt    3000
caaggaacac ctacaggtct tctgggatgg gtccttctgg aaacttagcc aaaatatttc    3060
tgagctaaaa gatggtgaat tgtggaataa attctttgtg cggattctga atgccaatga    3120
tgaggccaca gtgtctgttc ttggggagct tgcagcagaa atgaatgggg ttttgacac    3180 tacattccaa agtcacctga caaagccctt atggaaggta gggaagttaa ctagtcctgg    3240
ggctttgctc tttcagtgag ctaggcaatc aagtctcaca gattgctgcc tcagagcaat    3300
ggttgtattg tggaacactg aaactgtatg tgctgtaatt taatttagga cacatttaga    3360
tgcactacca ttgctgttct acttttggt acaggtatat tttgacgtca ctgatatttt    3420
ttatacagtg atatacttac tcatggcctt gtctaacttt tgtgaagaac tatttttattc    3480 taaacagact cattacaaat ggttaccttg ttatttaacc catttgtctc tacttttccc    3540
tgtacttttc ccatttgtaa tttgtaaaat gttctcttat gatcaccatg tattttgtaa    3600
ataataaaat agtatctgtt aaaaaaaaaa aaaaaaaaa aaaaaaaa                3649
```

<210> SEQ ID NO 17
<211> LENGTH: 3664
<212> TYPE: DNA
<213> ORGANISM: Artificial Sequence
<220> FEATURE:
<223> OTHER INFORMATION: Bub 1B mRNA sequences
<220> FEATURE:
<221> NAME/KEY: misc_feature
<222> LOCATION: (3520)..(3520)
<223> OTHER INFORMATION: n is a, c, g, or t

<400> SEQUENCE: 17

```
gttagggagt cgtgtgcgtg ccttggtcgc ttctgtagct ccgagggcag gttgcggaag      60
aaagcccagg cggtctgtgg cccagaagaa aggcctgcag caggacgagg acctgagcca     120
ggaatgcagg atggcggcgg tgaaaaagga aggggtgct ctgagtgaag ccatgtccct      180
ggagggagat gaatgggaac tgagtaaaga aaatgtacaa cctttaaggc aagggcggat    240
catgtccacg cttcagggag cactggcaca agaatctgcc tgtaacaata ctcttcagca    300
gcagaaacgg gcatttgaat atgaaattcg attttacact ggaaatgacc ctctggatgt    360
ttgggatagg tatatcagct ggacagagca gaactatcct caaggtggga aggagagtaa    420
tatgtcaacg ttattagaaa gagctgtaga agcactacaa ggagaaaaac gatattatag    480
```

```
tgatcctcga tttctcaatc tctggcttaa attagggcgt ttatgcaatg agcctttgga    540
tatgtacagt tacttgcaca accaagggat tggtgtttca cttgctcagt tctatatctc    600
atgggcagaa gaatatgaag ctagagaaaa ctttaggaaa gcagatgcga tatttcagga    660
agggattcaa cagaaggctg aaccactaga aagactacag tcccagcacc gacaattcca    720
agctcgagtg tctcggcaaa ctctgttggc acttgagaaa gaagaagagg aggaagtttt    780
tgagtcttct gtaccacaac gaagcacact agctgaacta aagagcaaag ggaaaaagac    840
agcaagagct ccaatcatcc gtgtaggagg tgctctcaag gctccaagcc agaacagagg    900
actccaaaat ccatttcctc aacagatgca aataatagt agaattactg tttttgatga    960
aaatgctgat gaggcttcta cagcagagtt gtctaagcct acagtccagc catggatagc   1020
acccccatg cccagggcca agagaatga gctgcaagca ggcccttgga acacaggcag   1080
gtccttggaa cacaggcctc gtggcaatac agcttcactg atagctgtac ccgctgtgct   1140
tcccagtttc actccatatg tggaagagac tgcacaacag ccagttatga caccatgtaa   1200
aattgaacct agtataaacc acatcctaag caccagaaag cctggaaagg aagaaggaga   1260
tcctctacaa agggttcaga gccatcagca agcatctgag gagaagaaag agaagatgat   1320
gtattgtaag gagaagattt atgcaggagt aggggaattc tcctttgaag aaattcgggc   1380
tgaagttttc cggaagaaat taaaagagca aagggaagcc gagctattga ccagtgcaga   1440
gaagagagca gaaatgcaga aacagattga agagatggag aagaagctaa agaaatccaa   1500
aactactcag caagaaagaa caggtgatca gcaagaagag acgatgccta caaaggagac   1560
aactaaactg caaattgctt ccgagtctca gaaaatacca ggaatgactc tatccagttc   1620
tgtttgtcaa gtaaactgtt gtgccagaga aacttcactt gcggagaaca tttggcagga   1680
acaacctcat tctaaaggtc ccagtgtacc tttctccatt tttgatgagt ttcttctttc   1740
agaaaagaag aacaaaagtc ctcctgcaga tcccccacga gttttagctc aacgaagacc   1800
ccttgcagtt ctcaaaacct cagaaagcat cacctcaaat gaagatgtgt ctccagatgt   1860
ttgtgatgaa tttacaggaa ttgaacccct gagcgaggat gccattatca caggcttcag   1920
aaatgtaaca atttgtccta acccagaaga cacttgtgac tttgccagag cagctcgttt   1980
tgtatccact ccttttcatg agataatgtc cttgaaggat ctcccttctg atcctgagag   2040
actgttaccg gaagaagatc tagatgtaaa gacctctgag gaccagcaga cagcttgtgg   2100
cactatctac agtcagactc tcagcatcaa gaagctgagc ccaattattg aagacagtcg   2160
tgaagccaca cactcctctg gcttctctgg ttcttctgcc tcggttgcaa gcacctcctc   2220
catcaaatgt cttcaaattc ctgagaaact agaacttact aatgagactt cagaaaaccc   2280
tactcagtca ccatggtgtt cacagtatcg cagacagcta ctgaagtccc taccagagtt   2340
aagtgcctct gcagagttgt gtatagaaga cagaccaatg cctaagttgg aaattgagaa   2400
ggaaattgaa ttaggtaatg aggattactg cattaaacga gaatacctaa tatgtgaaga   2460
ttacaagtta ttctgggtgg cgccaagaaa ctctgcagaa ttaacagtaa taaaggtatc   2520
ttctcaacct gtcccatggg acttttatat caacctcaag ttaaaggaac gtttaaatga   2580
agattttgat cattttgca gctgttatca atatcaagat ggctgtattg tttggcacca   2640
atatataaac tgcttcaccc ttcaggatct tctccaacac agtgaatata ttacccatga   2700
aataacagtg ttgattattt ataacctttt gacaatagtg gagatgctac acaaagcaga   2760
aatagtccat ggtgacttga gtccaaggtg tctgattctc agaaacagaa tccacgatcc   2820
ctatgattgt aacaagaaca atcaagcttt gaagatagtg gactttttcct acagtgttga   2880
```

```
ccttagggtg cagctggatg ttttttaccct cagcggcttt cggactgtac agatcctgga    2940
aggacaaaag atcctggcta actgttcttc tccctaccag gtagacctgt ttggtatagc    3000
agatttagca catttactat tgttcaagga acacctacag gtcttctggg atgggtcctt    3060
ctggaaactt agccaaaata tttctgagct aaaagatggt gaattgtgga ataaattctt    3120
tgtgcggatt ctgaatgcca atgatgaggc cacagtgtct gttcttgggg agcttgcagc    3180
aaaaatgaat ggggtttttg acactacatt ccaaagtcac ctgaacaagg ccttatggaa    3240
ggtagggaag ttaactagtc ctggggcttt gctctttcag tgagctaggc aatcaagtct    3300
cacagattgc tgcctcagag caatggttgt attgtggaac actgaaactg tatgtgctgt    3360 aatttaatt aggacacatt tagatgcact accgttgctg ttctactttt tggtacaggt    3420
atattttgac gtcctgatat tttttataca gtgatatact tactcctggc cttgtctaac    3480
ttttgtgaaa aactatttta ttctaaacag aatcattacn aatggttacc ttgttattta    3540
accatttgtt ctctactttt ccccgtactt ttcccatttg taatttgtta aatgttctct    3600
tatgatcacc atgtattttg taaataataa aatagtatct gttaaaaaaa aaaaaaaaa    3660 aaaa                                                                  3664

<210> SEQ ID NO 18
<211> LENGTH: 1431
<212> TYPE: DNA
<213> ORGANISM: Artificial Sequence
<220> FEATURE:
<223> OTHER INFORMATION: CENPA mRNA sequences

<400> SEQUENCE: 18
ccgtgaagtg ggcggagcga gcgatttgaa cgcgagcggc gcggacttct gccaagcacc      60
ggctcatgtg aggctcgcgg cacagcgttc tctgggctcc ccagaagcca gcctttcgct     120
cccggacccg gcagcccgag caggagccgt gggaccgggc gccagcaccc tctgcggcgt     180
gtcatgggcc cgcgccgccg gagccgaaag cccgaggccc cgaggaggcg cagcccgagc     240
ccgaccccga cccccggccc ctcccggcgg ggccccctcct taggcgcttc ctcccatcaa     300
cacagtcggc ggagacaagg ttggctaaag gagatccgaa agcttcagaa gagcacacac     360
ctcttgataa ggaagctgcc cttcagccgc ctggcaagag aaatatgtgt taaattcact     420
cgtggtgtgg acttcaattg gcaagcccag gccctattgg ccctacaaga ggcagcagaa     480
gcatttctag ttcatctctt tgaggacgcc tatctcctca ccttacatgc aggccgagtt     540
actctcttcc caaaggatgt gcaactggcc ggaggatcc ggggccttga ggagggactc     600
ggctgagctc ctgcacccag tgtttctgtc agtctttcct gctcagccag ggggatgat     660 accggggact ctccagagcc atgactagat ccaatggatt ctgcgatgct gtctggactt     720
tgctgtctct gaacagtatg tgtgtgttgc tttaaatatt ttctttttt ttgagaagga     780 gaagactgca tgactttcct ctgtaacaga ggtaatatat gagacaatca acaccgttcc     840
aaaggcctga aaataatttt cagataaaga gactccaagg ttgactttag tttgtgagtt     900
actcatgtga ctatttgagg attttgaaaa catcagattt gctgtggtat gggagaaaag     960
gctatgtact tattatttta gctctttctg taatatttac attttttacc atatgtacat    1020
ttgtactttt attttacaca taagggaaaa aataagacca ctttgagcag ttgcctggaa    1080
ggctgggcat ttccatcata tagacctctg cccttcagag tagcctcacc attagtggca    1140
gcatcatgta actgagtgga ctgtgcttgt caacggatgt gtagcttttc agaaacttaa    1200
```

```
ttggggatga atagaaaacc tgtaagcttt gatgttctgg ttacttctag taaattcctg    1260
tcaaaatcaa ttcagaaatt ctaacttgga gaatttaaca ttttactctt gtaaatcata    1320
gaagatgtat cataacagtt cagaattta aagtacattt tcgatgcttt tatgggtatt    1380
tttgtagttt ctttgtagag agataataaa aatcaaaata tttaatgaaa a            1431
```

<210> SEQ ID NO 19
<211> LENGTH: 1352
<212> TYPE: DNA
<213> ORGANISM: Artificial Sequence
<220> FEATURE:
<223> OTHER INFORMATION: CENPA mRNA sequences

<400> SEQUENCE: 19

```
cgtgaagtgg gcggagcgag cgatttgaac gcgagcggcg cggacttctg ccaagcaccg     60
gctcatgtga ggctcgcggc acagcgttct ctgggctccc cagaagccag cctttcgctc    120
ccggacccgg cagcccgagc aggagccgtg ggaccgggcg ccagcaccct ctgcggcgtg    180
tcatgggccc gcgccgccgg agccgaaagc ccgaggcccc gaggaggcgc agcccgagcc    240
cgaccccgac ccccgccccc tcccggcggg gcccctcctt aggcgcttcc tcccatcaac    300
acagtcggcg gagacaaggt tggctaaagg agatccgaaa gcttcagaag agcacacacc    360
tcttgataag gaagctgccc ttcagccgcc tggcagcaga agcatttcta gttcatctct    420
ttgaggacgc ctatctcctc accttacatg caggccgagt tactctcttc ccaaaggatg    480
tgcaactggc ccggaggatc cggggccttg aggagggact cggctgagct cctgcaccca    540
gtgtttctgt cagtctttcc tgctcagcca gggggggatga taccgggggac tctccagagc    600 catgactaga tccaatggat tctgcgatgc tgtctggact tgctgtctc tgaacagtat    660 gtgtgtgttg ctttaaatat tttctttttt tttgagaagg agaagactgc atgactttcc    720
tctgtaacag aggtaatata tgagacaatc aacaccgttc caaaggcctg aaaataattt    780
tcagataaag agactccaag gttgacttta gtttgtgagt tactcatgtg actatttgag    840
gattttgaaa acatcagatt tgctgtggta tgggagaaaa ggctatgtac ttattatttt    900
agctctttct gtaatattta catttttac catatgtaca tttgtacttt tatttttacac    960 ataagggaaa aaataagacc actttgagca gttgcctgga aggctgggca tttccatcat   1020
atagacctct gcccttcaga gtagcctcac cattagtggc agcatcatgt aactgagtgg   1080
actgtgcttg tcaacggatg tgtagctttt cagaaactta attggggatg aatagaaaac   1140
ctgtaagctt tgatgttctg gttacttcta gtaaattcct gtcaaaatca attcagaaat   1200
tctaacttgg agaattaac attttactct gtaaatcat agaagatgta tcataacagt    1260
tcagaatttt aaagtacatt ttcgatgctt ttatgggtat ttttgtagtt tctttgtaga   1320
gagataataa aaatcaaaat atttaatgaa aa                                 1352
```

<210> SEQ ID NO 20
<211> LENGTH: 2170
<212> TYPE: DNA
<213> ORGANISM: Artificial Sequence
<220> FEATURE:
<223> OTHER INFORMATION: NEK2 mRNA sequences

<400> SEQUENCE: 20

```
cggggcccaa ggcaggggtg gcgggtcagt gctgctcggg ggcttctcca tccaggtccc     60
tggagttcct ggtccctgga gctccgcact tggcggcgca acctgcgtga ggcagcgcga    120
ctctggcgac tggccggcca tgccttcccg ggctgaggac tatgaagtgt tgtacaccat    180
```

```
tggcacaggc tcctacgcc gctgccagaa gatccggagg aagagtgatg gcaagatatt      240
agtttggaaa gaacttgact atggctccat gacagaagct gagaaacaga tgcttgtttc      300
tgaagtgaat ttgcttcgtg aactgaaaca tccaaacatc gttcgttact atgatcggat      360
tattgaccgg accaatacaa cactgtacat tgtaatggaa tattgtgaag gaggggatct      420
ggctagtgta attacaaagg gaaccaagga aaggcaatac ttagatgaag agtttgttct      480
tcgagtgatg actcagttga ctctggccct gaaggaatgc cacagacgaa gtgatggtgg      540
tcataccgta ttgcatcggg atctgaaacc agccaatgtt ttcctggatg gcaagcaaaa      600
cgtcaagctt ggagactttg gctagctag aatattaaac catgcacga gttttgcaaa       660 aacatttgtt ggcacacctt attacatgtc tcctgaacaa atgaatcgca tgtcctacaa      720
tgagaaatca gatatctggt cattgggctg cttgctgtat gagttatgtg cattaatgcc      780
tccatttaca gcttttagcc agaaagaact cgctgggaaa atcagagaag gcaaattcag      840
gcgaattcca taccgttact ctgatgaatt gaatgaaatt attacgagga tgttaaactt      900
aaaggattac catcgaccct ctgttgaaga aattcttgag aaccctttaa tagcagattt      960
ggttgcagac gagcaaagaa gaaatcttga gagaagaggg cgacaattag agagccaga     1020 aaaatcgcag gattccagcc ctgtattgag tgagctgaaa ctgaaggaaa ttcagttaca     1080
ggagcgagag cgagctctca agcaagaga agaaagattg gagcagaaag acaggagct       1140 tgtgttcgt gagagactag cagaggacaa actggctaga gcagaaaatc tgttgaagaa      1200
ctacagcttg ctaaaggaac ggaagttcct gtctctggca agtaatccag aacttcttaa     1260
tcttccatcc tcagtaatta agaagaaagt tcatttcagt ggggaaagta aagagaacat     1320
catgaggagt gagaattctg agagtcagct cacatctaag tccaagtgca aggacctgaa     1380
gaaaaggctt cacgctgccc agctgcgggc tcaagccctg tcagatattg agaaaaatta     1440
ccaactgaaa agcagacaga tcctgggcat gcgctagcca ggtagagaga cacagagctg     1500
tgtacaggat gtaatattac caacctttaa agactgatat tcaaatgctg tagtgttgaa     1560
tacttggttc catgagccat gccttctgt atagtacaca tgatatttcg gaattggttt      1620
tactgttctt cagcaactat tgtacaaaat gttcacattt aatttttctt tcttcttta      1680 agaacatatt ataaaagaa tactttcttg gttgggcttt taatcctgtg tgtgattact      1740
agtaggaaca tgagatgtga cattctaat cttgggagaa aaaataatgt taggaaaaaa     1800
atatttatgc aggaagagta gcactcactg aatagtttta aatgactgag tggtatgctt     1860
acaattgtca tgtctagatt taaattttaa gtctgagatt ttaaatgttt ttgagcttag     1920
aaaacccagt tagatgcaat ttggtcatta ataccatgac atcttgctta taaatattcc     1980
attgctctgt agttcaaatc tgttagcttt gtgaaaattc atcactgtga tgtttgtatt     2040
cttttttttt tttctgttta acagaatatg agctgtctgt catttaccta cttctttccc     2100
actaaataaa agaattcttc agtttccctg taaaaaaaaa aaaaaaaaa aaaaaaaaa      2160 aaaaaaaaaa                                                           2170
```

<210> SEQ ID NO 21
<211> LENGTH: 1019
<212> TYPE: DNA
<213> ORGANISM: Artificial Sequence
<220> FEATURE:
<223> OTHER INFORMATION: NEK2 mRNA sequences

<400> SEQUENCE: 21

```
aacgggccc aaggcagggg tggcgggtca gtgctgctcg ggggcttctc catccaggtc      60
cctggagttc ctggtccctg gagctccgca cttggcggcg caacctgcgt gaggcagcgc     120
gactctggcg actggccggc catgccttcc cgggctgagg actatgaagt gttgtacacc    180
attggcacag gctcctacgg ccgctgccag aagatccgga ggaagagtga tgcaagata     240 ttagtttgga aagaacttga ctatggctcc atgacagaag ctgagaaaca gatgcttgtt    300
tctgaagtga atttgcttcg tgaactgaaa catccaaaca tcgttcgtta ctatgatcgg    360
attattgacc ggaccaatac aacactgtac attgtaatgg aatattgtga aggaggggat    420
ctggctagtg taattacaaa gggaaccaag gaaaggcaat acttagatga agagtttgtt   480
cttcgagtga tgactcagtt gactctggcc ctgaaggaat gccacagacg aagtgatggt    540
ggtcataccg tattgcatcg ggatctgaaa ccagccaatg ttttcctgga tgcaagcaa    600 aacgtcaagc ttggagactt tgggctagct agaatattaa accacgacac gagttttgca    660
aaaacatttg ttggcacacc ttattacatg tctcctgaac aaatgaatcg catgtcctac    720
aatgagaaat cagatatctg gtcattgggc tgcttgctgt atgagttatg tgcattaatc    780
ttttagccag aaagaactcg ctgggaaaat cagagaaggc aaattcaggc gaattccata    840
ccgttactct gatgaattga atgaaattat tacgaggatg ttaaacttaa aggattacca    900
tcgaccttct gttgaagaaa ttcttgagaa ccctttaata gcagatttgg ttgcagacga    960
gcaaagaaga aatcttgaga gaagagggcg acaattagga gagccagaaa aaaaaaaaa   1019

<210> SEQ ID NO 22
<211> LENGTH: 3079
<212> TYPE: DNA
<213> ORGANISM: Artificial Sequence
<220> FEATURE:
<223> OTHER INFORMATION: RACGAP1 mRNA sequences

<400> SEQUENCE: 22
ccacgcgtcc ggcggagcga agtgaagggt ggcccaggtg gggccaggct gactgaaaaa     60
gatggatact atgatgctga atgtgcggaa tctgtttgag cagcttgtgc gccgggtgga    120
gattctcagt gaaggaaatg aagtccaatt tatccagttg gcgaaggact ttgaggattt    180
ccgtaaaaag tggcagagga ctgaccatga gctggggaaa tacaaggatc ttttgatgaa    240
agcagagact gagcgaagtg ctctggatgt taagctgaag catgcacgta atcaggtgga    300
tgtagagatc aaacggagac agagagctga ggctgactgc gaaaagctgg aacgacagat    360
tcagctgatt cgagagatgc tcatgtgtga cacatctggc agcattcaac taagcgagga    420
gcaaaaatca gctctggctt ttctcaacag aggccaacca tccagcagca atgctgggaa    480
caaaagacta tcaaccattg atgaatctgg ttccatttta tcagatatca gctttgacaa    540
gactgatgaa tcactggatt gggactcttc tttggtgaag actttcaaac tgaagaagag    600
agaaaagagg cgctctacta gccgacagtt tgttgatggt cccctggac ctgtaaagaa     660 aactcgttcc attggctctg cagtagacca gggaatgaa tccatagttg caaaaactac     720
agtgactgtt cccaatgatg gcgggcccat cgaagctgtg tccactattg agactgtgcc    780
atattggacc aggagccgaa ggaaaacagg tactttacaa ccttggaaca gtgactccac    840
cctgaacagc aggcagctgg agccaagaac tgagacagac agtgtgggca cgccacagag    900
taatggaggg atgcgcctgc atgactttgt ttctaagacg gttattaaac ctgaatcctg    960
tgttccatgt ggaagcgga taaaattgg caaattatct ctgaagtgtc gagactgtcg    1020
tgtggtctct catccagaat gtcgggaccg ctgtcccctt ccctgcattc ctaccctgat   1080
```

```
aggaacacct gtcaagattg gagagggaat gctggcagac tttgtgtccc agacttctcc   1140
aatgatcccc tccattgttg tgcattgtgt aaatgagatt gagcaaagag gtctgactga   1200
gacaggcctg tataggatct ctggctgtga ccgcacagta aaagagctga agagaaatt    1260 cctcagagtg aaaactgtac ccctcctcag caaagtggat gatatccatg ctatctgtag   1320
ccttctaaaa gactttcttc gaaacctcaa agaacctctt ctgacctttc gccttaacag   1380
agcctttatg gaagcagcag aaatcacaga tgaagacaac agcatagctg ccatgtacca   1440
agctgttggt gaactgcccc aggccaacag ggacacatta gctttcctca tgattcactt   1500
gcagagagtg gctcagagtc cacatactaa aatggatgtt gccaatctgg ctaaagtctt   1560
tggccctaca atagtggccc atgctgtgcc caatccagac ccagtgacaa tgttacagga   1620
catcaagcgt caacccaagg tggttgagcg cctgctttcc ttgcctctgg agtattggag   1680
tcagttcatg atggtggagc aagagaacat tgacccccta catgtcattg aaaactcaaa   1740
tgccttttca acaccacaga caccagatat taaagtgagt ttactgggac tgtgaccac    1800 tcctgaacat cagcttctca agactccttc atctagttcc ctgtcacaga gagtccgttc   1860
caccctcacc aagaacactc ctagatttgg gagcaaaagc aagtctgcca ctaacctagg   1920
acgacaaggc aactttttg  cttctccaat gctcaagtga agtcacatct gcctgttact    1980
tcccagcatt gactgactat aagaaaggac acatctgtac tctgctctgc agcctcctgt   2040
actcattact acttttagca ttctccaggc ttttactcaa gtttaattgt gcatgagggt   2100
tttattaaaa ctatatatat ctccccttcc ttctcctcaa gtcacataat atcagcactt   2160
tgtgctggtc attgttggga gcttttagat gagacatctt tccagggta gaagggttag    2220 tatggaattg gttgtgattc ttttttggga agggggttat tgttcctttg gcttaaagcc   2280
aaatgctgct catagaatga tctttctcta gtttcattta gaactgattt ccgtgagaca   2340
atgacagaaa ccctacctat ctgataagat tagcttgtct cagggtggga agtgggaggg   2400
cagggcaaag aaaggattag accagaggat ttaggatgcc tccttctaag aaccagaagt   2460
tctcattccc cattatgaac tgagctataa tatggagctt tcataaaaat gggatgcatt   2520
gaggacagaa ctagtgatgg gagtatgcgt agctttgatt tggatgatta ggtctttaat   2580
agtgttgagt ggcacaacct tgtaaatgtg aaagtacaac tcgtatttat ctctgatgtg   2640
ccgctggctg aactttgggt tcatttgggg tcaaagccag tttttctttt aaaattgaat   2700
tcattctgat gcttggcccc catacccca accttgtcca gtggagccca acttctaaag    2760
gtcaatatat catcctttgg catcccaact aacaataaag agtaggctat aagggaagat   2820
tgtcaatatt ttgtggtaag aaaagctaca gtcattttt ctttgcactt tggatgctga    2880
aatttttccc atggaacata gccacatcta gatagatgtg agcttttct tctgttaaaa    2940 ttattcttaa tgtctgtaaa aacgattttc ttctgtagaa tgtttgactt cgtattgacc   3000
cttatctgta aaacacctat ttgggataat atttggaaaa aaagtaaata gcttttttcaa  3060 aatgaaaaaa aaaaaaaaa                                                3079
```

<210> SEQ ID NO 23
<211> LENGTH: 3045
<212> TYPE: DNA
<213> ORGANISM: Artificial Sequence
<220> FEATURE:
<223> OTHER INFORMATION: RACGAP1 mRNA sequences

<400> SEQUENCE: 23

```
gaccaggtgc gtctgccgct ggattgtgat aggaagcaga gtgttcgtgt gaaagatgga    60
tactatgatg ctgaatgtgc ggaatctgtt tgagcagctt gtgcgccggg tggagattct   120
cagtgaagga aatgaagtcc aatttatcca gttggcgaag gactttgagg atttccgtaa   180
aaagtggcag aggactgacc atgagctggg gaaatacaag gatcttttga tgaaagcaga   240
gactgagcga agtgctctgg atgttaagct gaagcatgca cgtaatcagg tggatgtaga   300
gatcaaacgg agacagagag ctgaggctga ctgcgaaaag ctggaacgac agattcagct   360
gattcgagag atgctcatgt gtgacacatc tggcagcatt caactaagcg aggagcaaaa   420
atcagctctg gcttttctca acagaggcca accatccagc agcaatgctg ggaacaaaag   480
actatcaacc attgatgaat ctggttccat tttatcagat atcagctttg acaagactga   540
tgaatcactg gattgggact cttcttggtg aagactttca aactgaagaa gagagaaaag   600
aggcgctcta ctagccgaca gtttgttgat ggtcccctg gacctgtaaa gaaaactcgt   660
tccatttggc tctgcagtag accagggaa tgaatccata gttgcaaaaa ctacagtgac   720
tgttcccaat gatggcggc ccatcgaagc tgtgtccact attgagactg tgccatattg   780
gaccaggagc cgaaggaaaa caggtacttt acaaccttgg aacagtgact ccaccctgaa   840
cagcaggcag ctggagccaa gaactgagac agacagtgtg ggcacgccac agagtaatgg   900
agggatgcgc ctgcatgact ttgttttctaa gacggttatt aaacctgaat cctgtgttcc   960
atgtggaaag cggataaaat ttggcaaatt atctctgaag tgtcgagact gtcgtgtggt  1020
ctctcatcca gaatgtcggg accgctgtcc ccttccctgc attcctaccc tgataggaac  1080
acctgtcaag attggagagg gaatgctggc agactttgtg tcccagactt ctccaatgat  1140
cccctccatt gttgtgcatt gtgtaaatga gattgagcaa agaggtctga ctgagacagg  1200
cctgtatagg atctctggct gtgaccgcac agtaaaagag ctgaaagaga aattcctcag  1260
agtgaaaact gtaccctcc tcagcaaagt ggatgatatc catgctatct gtagccttct  1320
aaaagacttt cttcgaaacc tcaaagaacc tcttctgacc ttttcgcctt aacagagcct  1380
ttatggaagc agcagaaatc acagatgaag acaacagcat agctgccatg taccaagctg  1440
ttggtgaact gccccaggcc aacagggaca cattagcttt cctcatgatt cacttgcaga  1500
gagtggctca gagtccacat actaaaatgg atgttgccaa tctggctaaa gtctttggcc  1560
ctacaatagt ggcccatgct gtgcccaatc cagacccagt gacaatgtta caggacatca  1620
agcgtcaacc caaggtggtt gagcgcctgc tttccttgcc tctggagtat tggagtcagt  1680
tcatgatggt ggagcaagag aacattgacc ccctacatgt cattgaaaac tcaaatgcct  1740
tttcaacacc acagacacca gatattaaag tgagtttact gggacctgtg accactcctg  1800
aacatcagct tctcaagact ccttcatcta gttccctgtc acagagagtc cgttccaccc  1860
tcaccaagaa cactcctaga tttgggagca aaagcaagtc tgccactaac ctaggacgac  1920
aaggcaactt ttttgcttct ccaatgctca agtgaagtca catctgcctg ttacttccca  1980
gcattgactg actataagaa aggacacatc tgtactctgc tctgcagcct cctgtactca  2040
ttactacttt tagcattctc caggctttta ctcaagttta attgtgcatg agggttttat  2100
taaaactata tatatctccc cttccttctc ctcaagtcac ataatatcag cactttgtgc  2160
tggtcattgt tgggagcttt tagatgagac atctttccag gggtagaagg gttagtatgg  2220
aattggttgt gattctttt ggggaagggg gttattgttc ctttggctta aagccaaatg  2280
ctgctcatag aatgatcttt ctctagtttc atttagaact gatttccgtg agacaatgac  2340
agaaacccta cctatctgat aagattagct tgtctcaggg tgggaagtgg gagggcaggg  2400
```

-continued

```
caaagaaagg attagaccag aggatttagg atgcctcctt ctaagaacca gaagttctca    2460
ttccccatta tgaactgagc tataatatgg agctttcata aaaatgggat gcattgagga    2520
cagaactagt gatgggagta tgcgtagctt tgatttggat gattaggtct ttaatagtgt    2580
tgagtggcac aaccttgtaa atgtgaaagt acaactcgta tttatctctg atgtgccgct    2640
ggctgaactt tggggttcatt tggggtcaaa gccagttttt cttttaaaat tgaattcatt    2700
ctgatgcttg gcccccatac ccccaacctt gtccagtgga gcccaacttc taaaggtcaa    2760
tatatcatcc tttggcatcc caactaacaa taaagagtag gctataaggg aagattgtca    2820
atattttgtg gtaagaaaag ctacagtcat tttttctttg cactttggat gctgaaattt    2880
ttcccatgga acatagccac atctagatag atgtgagctt tttcttctgt taaaattatt    2940
cttaatgtct gtaaaaacga ttttcttctg tagaatgttt gacttcgtat tgacccttat    3000
ctgtaaaaca cctatttggg ataaaaaaaa aaaaaaaaaa aaaaa             3045

<210> SEQ ID NO 24
<211> LENGTH: 2500
<212> TYPE: DNA
<213> ORGANISM: Artificial Sequence
<220> FEATURE:
<223> OTHER INFORMATION: RRM2 mRNA sequences

<400> SEQUENCE: 24
cccaggcgca gccaatggga agggtcggag gcatggcaca gccaatggga agggccgggg      60
caccaaagcc aatgggaagg gccgggagcg cgcggcgcgg gagatttaaa ggctgctgga     120
gtgaggggtc gcccgtgcac cctgtcccag ccgtcctgtc ctggctgctc gctctgcttc     180
gctgcgcctc cactatgctc tccctccgtg tcccgctcgc gcccatcacg gacccgcagc     240
agctgcagct ctcgccgctg aagggctca gcttggtcga caaggagaac acgccgccgg     300
ccctgagcgg gacccgcgtc ctggccagca agaccgcgag gaggatcttc caggagccca     360
cggagccgaa aactaaagca gctgcccccg gcgtggagga tgagccgctg ctgagagaaa     420 accccccgccg ctttgtcatc ttccccatcg agtaccatga tatctggcag atgtataaga     480
aggcagaggc ttccttttgg accgccgagg aggttgacct ctccaaggac attcagcact     540
gggaatccct gaaacccgag gagagatatt ttatatccca tgttctggct ttctttgcag     600
caagcgatgg catagtaaat gaaaacttgg tggagcgatt tagccaagaa gttcagatta     660
cagaagcccg ctgtttctat ggcttccaaa ttgccatgga aaacatacat tctgaaatgt     720
atagtcttct tattgacact tacataaaag atcccaaaga aagggaattt ctcttcaatg     780
ccattgaaac gatgccttgt gtcaagaaga ggcagactg ggccttgcgc tggattgggg     840
acaaagaggc tacctatggt gaacgtgttg tagcctttgc tgcagtggaa gcatttttct     900
tttccggttc ttttgcgtcg atattctggc tcaagaaacg aggactgatg cctggcctca     960
cattttctaa tgaacttatt agcagagatg agggtttaca ctgtgatttt gcttgcctga    1020
tgttcaaaca cctggtacac aaaccatcgg aggagagagt aagagaaata attatcaatg    1080
ctgttcggat agaacaggag ttcctcactg aggccttgcc tgtgaagctc attgggatga    1140
attgcactct aatgaagcaa tacattgagt ttgtggcaga cagacttatg ctggaactgg    1200
gttttagcaa ggttttcaga gtagagaacc catttgactt tatggagaat atttcactgg    1260
aaggaaagac taacttcttt gagaagagag taggcgagta tcagaggatg ggagtgatgt    1320
caagtccaac agagaattct tttaccttgg atgctgactt ctaaatgaac tgaagatgtg    1380
```

-continued

```
cccttacttg gctgattttt ttttttccatc tcataagaaa aatcagctga agtgttacca    1440
actagccaca ccatgaattg tccgtaatgt tcattaacag catctttaaa actgtgtagc    1500
tacctcacaa ccagtcctgt ctgtttatag tgctggtagt atcaccttt gccagaaggc    1560 ctggctggct gtgacttacc atagcagtga caatggcagt cttggcttta aagtgagggg    1620 tgaccctta gtgagcttag cacagcggga ttaaacagtc ctttaaccag cacagccagt    1680
taaaagatgc agcctcactg cttcaacgca gattttaatg tttacttaaa tataaacctg    1740
gcactttaca aacaaataaa cattgttttg tactcacggc ggcgataata gcttgattta    1800
tttggtttct acaccaaata cattctcctg accactaatg ggagccaatt cacaattcac    1860
taagtgacta aagtaagtta aacttgtgta gactaagcat gtaattttta agttttattt    1920
taatgaatta aaatatttgt taaccaactt taaagtcagt cctgtgtata cctagatatt    1980
agtcagttgg tgccagatag aagacaggtt gtgttttat cctgtggctt gtgtagtgtc    2040
ctgggattct ctgcccctc tgagtagagt gttgtgggat aaaggaatct ctcagggcaa    2100
ggagcttctt aagttaaatc actagaaatt tagggtgat ctgggccttc atatgtgtga    2160
gaagccgttt catttatt ctcactgtat tttcctcaac gtctggttga tgagaaaaaa    2220
ttcttgaaga gttttcatat gtgggagcta aggtagtatt gtaaatttc aagtcatcct    2280 taaacaaaat gatccaccta agatcttgcc cctgttaagt ggtgaaatca actagaggtg    2340
gttcctacaa gttgttcatt ctagttttgt ttggtgtaag taggttgtgt gagttaattc    2400
atttatattt actatgtctg ttaaatcaga aattttttat tatctatgtt cttctagatt    2460
ttacctgtag ttcataaaaa aaaaaaaaaa aaaaaaaaa                            2500
```

<210> SEQ ID NO 25
<211> LENGTH: 1649
<212> TYPE: DNA
<213> ORGANISM: Artificial Sequence
<220> FEATURE:
<223> OTHER INFORMATION: RRM2 mRNA sequences

<400> SEQUENCE: 25

```
ccgtcctgtc ctggctgctc gctctgcttc gctgcgccgc cactatgctc tccctccgtg      60
tcccgctcgc gcccatcacg gacccgcagc agctgcagct ctcgccgctg aagggcctca    120
gcttggtcga caaggagaac acgccgccgg ccctgagcgg gacccgcgtc ctggccagca    180
agaccgcgag gaggatcttc caggagccca cggagccgaa aactaaagca gctgcccccg    240
gcgtggagga tgagccgctg ctgagagaaa accccgccg ctttgtcatc ttccccatcg    300
agtaccatga tatctggcag atgtataaga aggcagaggc ttcctttgg accgccgagg    360 aggtggacct ctccaaggac attcagcact gggaatccct gaaacccgag gagagatatt    420
ttatatccca tgttctggct ttcttttgcag caagcgatgg catagtaaat gaaaacttgg    480
tggagcgatt tagccaagaa gttcagatta cagaagcccg ctgtttctat ggcttccaaa    540
ttgccatgga aaacatacat tctgaaatgt atagtcttct tattgacact acataaaaag    600
atcccaaaga aagggaattt ctcttcaatg ccattgaaac gatgccttgt gtcaagaaga    660
aggcagactg ggccttgcgc tggattggg acaaagaggc tacctatggt gaacgtgttg    720
tagcctttgc tgcagtggaa ggcatttctct tttccggttc ttttgcgtcg atattctggc    780
tcaagaaacg aggactgatg cctggcctca cattttctaa tgaacttatt agcagagatg    840
agggtttaca ctgtgatttt gcttgcctga tgttcaaaca cctggtacac aaaccatcgg    900
aggagagagt aagagaaata attatcaatg ctgttcggat agaacaggag ttcctcactg    960
```

```
aggccttgcc tgtgaagctc attgggatga attgcactct aatgaagcaa tacattgagt    1020
ttgtggcaga cagacttatg ctggaactgg gttttagcaa ggttttcaga gtagagaacc    1080
catttgactt tatggagaat atttcactgg aaggaaagac taacttcttt gagaagagag    1140
taggcgagta tcagaggatg ggagtgatgt caagtccaac agagaattct tttaccttgg    1200
atgctgactt ctaaatgaac tgaagatgtg cccttacttg gctgattttt tttttccatc    1260
tcataagaaa aatcagctga agtgttacca actagccaca ccatgaattg tccgtaatgt    1320
tcattaacag catctttaaa actgtgtagc tacctcacaa ccagtcctgt ctgtttatag    1380
tgctggtagt atcaccttt  gccagaaggc ctggctggct gtgacttacc atagcagtga    1440
caatggcagt cttggcttta aagtgagggg tgacccttta gtgagcttag cacagcggga    1500
ttaaacagtc ctttaaccag cacagccagt taaaagatgc agcctcactg cttcaacgca    1560
gattttaatg tttacttaaa tataaacctg gcactttaca aacaaataaa cattgtttgt    1620
actcacaaaa aaaaaaaaaa aaaaaaaaa                                      1649
```

TUMOR GRADING AND CANCER PROGNOSIS

RELATED APPLICATIONS

This application claims benefit of priority from International Application No. PCT/US2008/075528, filed on Sep. 6, 2008 with designation of the U.S., which claims priority to U.S. Provisional Patent Application No. 60/970,529, filed Sep. 6, 2007. Both applications are hereby incorporated by reference as if fully set forth.

FIELD OF THE DISCLOSURE

The disclosure relates to the identification and use of gene expression profiles, or patterns, with clinical relevance to cancer. In particular, the disclosure is based in part on the identities of genes that are expressed in correlation with tumor grade. The levels of gene expression form a molecular index that is able to determine tumor grade in a patient and predict clinical outcome, and so prognosis for a patient. The molecular grading of cancer may optionally be used in combination with a second molecular index for diagnosing cancer and its prognosis.

The gene expression profiles, whether embodied in nucleic acid expression, protein expression, or other expression formats, may be used to predict the clinical outcome of subjects afflicted with cancer, predict cancer recurrence, and/or predict occurrence of metastatic cancer. The profiles may also be used in the study and/or diagnosis of cancer cells and tissue as well as for the study of a subject's prognosis. When used for diagnosis or prognosis, the profiles are used to determine the treatment of cancer based upon the likelihood of life expectancy, cancer recurrence, and/or cancer metastasis.

BACKGROUND OF THE DISCLOSURE

Genome-wide expression profiling studies have created a "small flood" of prognostic gene signatures for breast cancer. An important issue is whether these signatures overlap in the prognostic space and whether combining several of them would provide more accurate prognosis. In one comparative study, four signatures (the intrinsic subtypes, 70-gene signature, wound response signature and Recurrence Score), developed using different patient cohorts and methodologies, were found to be highly concordant in classifying patients into low and high risk groups. Furthermore, combining these signatures did not yield significant improvement in predictive accuracy, suggesting that the prognostic information space spanned by these signatures are largely overlapping.

The prognostic importance of tumor grade has also been established (Cianfrocca et al., *Oncologist* 9:606-16 (2004)). Various molecular indices for cancer prognosis have been previously reported. Examples include a genomic grade index (GGI) based on 97 tumor grade-associated genes, which has been shown to be strongly prognostic (Sotiriou et al., *J. Natl. Cancer Inst.*, 98:262-72 (2006)); a 70-gene signature (van 't Veer et al., *Nature*, 415:530-6 (2002)); and the Oncotype DX 21-gene recurrence score algorithm (Paik et al., *NE J. Med.*, 351:2817-26 (2004)).

The 97-gene tumor grade signature was reported to be comparable to the 70-gene signature and Recurrence Score algorithm in independent cohorts, and it has been hypothesized that most of the prognostic power of these signatures comes from genes associated with cellular proliferation.

A comparison of the above described signatures suggests that tumor grade-related genes are common denominators of these signatures (see for example, Sotiriou et al. supra., Desmedt et al., *Cell Cycle* 5:2198-202 (2006); Loi et al., *J. Clin. Oncol.*, 25:1239-46 (2007); and Sotiriou et al., *Nat. Rev. Cancer* 7:545-53 (2007)).

More recently, a 186-gene "invasiveness gene signature" (IGS), derived by comparing tumorigenic CD44+CD24−/low breast cancer cells with normal breast epithelium, has been proposed to extend beyond the proliferation-based prognostic space. However, a careful examination suggests that it too may derive its prognostic capacity from proliferation-related genes since IGS is highly correlated with a tumor grade signature (r=0.81).

Given the importance of tumor grade in prognosis and the existence of hundreds of genes whose expression levels highly correlate with tumor grade and proliferation, it may not be surprising that a multitude of seemingly distinct prognostic signatures could be developed. Furthermore, the prognostic robustness and redundancy of these genes suggest that a much simpler assay involving a few genes may be sufficient. For example, it has been noted that only a fraction of the 97 genes for GGI are needed for prognosis. In an independent study, Ivshina et al. also demonstrated that a 264-gene tumor grade signature can be reduced to 6 genes in silico (Ivshina et al., *Cancer Res.*, 66:10292-301 (2006)).

The citation of documents herein is not to be construed as reflecting an admission that any is relevant prior art. Moreover, their citation is not an indication of a search for relevant disclosures. All statements regarding the dates or contents of the documents is based on available information and is not an admission as to their accuracy or correctness.

BRIEF SUMMARY OF THE DISCLOSURE

The disclosure is based in part on the discovery and determination of gene expression levels in tumor cells that are correlated with tumor grade. In addition to use of the expression levels of the identified genes as a tumor grade signature, the expression levels may be used to provide prognostic information, such as cancer recurrence, and predictive information, such as responsiveness to certain therapies.

One gene identified by the disclosure encodes Bub1B ("budding uninhibited by benzimidazoles 1 beta) or p21 protein-activated kinase 6 (PAK6). Therefore, and in a first aspect of the disclosure, compositions and methods are described for the use of Bub1B gene expression to study or determine tumor grade, to provide prognostic information, and/or provide predictions of clinical responsiveness. In some cases, the determination is made with tumor cells from a subject to arrive at a diagnosis corresponding to that of a Grade I, Grade III, or intermediate grade tumor. Non-limiting examples of cells for use in the disclosure include those freshly isolated from the subject, those frozen after isolation, and those that are fixed and/or embedded, such as formalin fixed, paraffin embedded (FFPE). In some embodiments, the cells are breast cells, such as breast cancer cells.

In a second aspect, compositions and methods are disclosed for the use of four other gene expression levels to determine tumor grade, to provide prognostic information, and/or provide predictions of clinical responsiveness. These additional genes encode CENPA (centromere protein A, isoform a), NEK2 (NIMA-related kinase 2 or "never in mitosis gene a"-related kinase 2), RACGAP1 (Rac GTPase activating protein 1), and RRM2 (ribonucleotide reductase M2). Thus the disclosure is based in part on the discovery of five genes, the expression levels of which are useful for the determination of tumor grade in a cancer afflicted subject and for providing prognostic and predictive determinations for the subject.

While the expression level of each of these five genes may be used alone in the study or determination of tumor grade or to provide additional information, a third aspect of the disclosure includes the use of any combination of the five disclosed genes. So in some embodiments, a combination of expression levels of Bub1B and any one, two, or three of these additional four genes may be used. Similarly, a combination of expression levels of CENPA and any one, two, or three of Bub1B, NEK2, RACGAP1, or RRM2; of NEK2 and any one, two, or three of Bub1B, CENPA, RACGAP1, or RRM2; of RACGAP1 and any one, two, or three of Bub1B, CENPA, NEK2, or RRM2; of RRM2 and any one, two, or three of Bub1B, CENPA, NEK2, or RACGAP1 may be used.

In one embodiment, a combination of all five expression levels, as a 5-gene tumor grade signature (or molecular grade index) is disclosed. This index, or MGI, is able to recapitulate tumor grade and predict clinical outcome with comparable performance to the 97-gene GGI in two independent cohorts. MGI also serves as a prognostic factor for cancer recurrence and/or survival outcome.

In a further aspect, the disclosure includes the use of the 5-gene MGI in combination with a second molecular index for cancer. In one embodiment, the combination is of the second molecular index with all five of the disclosed genes. In other embodiments, the combination may be with any one, two, three, or four of the five disclosed genes as described herein. In some cases, the second molecular index is one based on the expression levels of two genes HoxB13 and IL17BR. In particular, a two-gene ratio of HoxB13 expression to IL17BR expression (or HoxB13:IL17BR ratio) may be used as the second molecular index (see US 2005/0239079 A1; US 2005/0239083 A1; and US 2006/0154267 A1). In an alternative embodiment, the second index may be a two-gene ratio of HoxB13 expression to CHDH expression.

The HoxB13:IL17BR (H:I) ratio was discovered based upon a study of novel biomarkers predictive of clinical outcome beyond standard prognostic factors. Patients who developed cancer recurrences were matched to those who did not with respect to tumor stage and grade. The simple H:I ratio was found to be suitable for predicting cancer recurrence in patients with estrogen receptor-positive (ER+) breast cancer receiving adjuvant tamoxifen therapy. Subsequent studies (Ma et al., *J. Clin. Oncol.*, 24:4611-9 (2006); Goetz et al., *Clin Cancer Res.* 12:2080-7 (2006); Jerevall et al., *Breast Cancer Res. Treat* (2007); Jansen et al., *J. Clin. Oncol.* 25:662-8 (2007)) have further shown that the ratio is both prognostic, such as by being an indicator of tumor aggressiveness, and predictive of tamoxifen benefit (i.e., tamoxifen response/resistance) within both retrospective and randomized clinical trials.

When both the disclosed 5-gene MGI and H:I ratio were analyzed using real-time reverse transcription-polymerase chain reaction (RT-PCR), the combination was found to provide superior stratification of risk of recurrence to that possible by either alone. This reflects an unexpected discovery because it indicates that the H:I ratio is independent of tumor grade. As such, the combination of the two indices improves cancer diagnosis and allows more accurate determination of its prognosis by efficiently analyzing independent parameters relevant to cancer.

In alternative embodiments, expression of one or more of the disclosed 5-gene signature may be used in combination with other genes or another molecular index for cancer prognosis. Non-limiting examples include the genomic grade index (GGI) based on 97 tumor grade-associated genes (Sotiriou et al., supra) and a subset of genes within those 97 genes; the MammaPrint 70-gene signature (van 't Veer et al., supra) and a subset of genes within those 70 genes; the Oncotype DX 21-gene recurrence score algorithm (Paik et al., supra) and a subset of genes within those 21 genes; and the Veridex 76 gene assay (Wang et al. *Lancet*, 365(9460):671-679 (2005)) and a subset of genes within those 76 genes. In other cases, expression of one or more of the disclosed 5-gene tumor grade signature may be used in combination with the expression level(s) of one or more genes expressed in correlation with a proliferation phenotype. In some cases, genes expressed in correlation with a proliferation phenotype are within the sets of 97, 70, 21, and 76 genes as described above. Non-limiting examples of genes expressed in correlation with a proliferation phenotype are Ki-67, STK15, Survivin, Cyclin B1, and MYBL2. So the expression level(s) of any one, two, three, or four of the five MGI genes may be used with other genes or another molecular index for cancer prognosis or as a predictor of clinical outcome. Of course the expression levels of all five genes, as an MGI, may also be used in combination with additional genes or another index as described above and hereafter. Additionally, a combination of expression levels of one, some, or all, of the MGI genes with additional genes may also be further combined with the H:I ratio as described above and hereafter as a prognostic factor or a predictor of clinical outcome.

So embodiments of the disclosure include methods that assaying for the expression of one, some, or all of the MGI genes, optionally with one or more additional genes as described above, and optionally in combination with the H:I ratio, as a prognostic factor or a predictor of treatment outcome. Such an assay method may be used to stratify ER+ subjects for prognostic value and for predictive value. As a prognostic, the stratification may be based on differential expression levels that correlate with, and so indicate, tumor aggressiveness as a non-limiting example. As a predictor, the stratification may be based on differential expression levels that correlate with, and so indicate, chemotherapy responsiveness (or sensitivity) and/or non-responsiveness (or resistance), which may also be considered as a predictor of chemotherapy benefit. As a non-limiting example, the stratification (based on expression levels) may be used to predict endocrine resistance (such as resistance to tamoxifen as a non-limiting example) and/or prediction of benefit from inhibitors that target endocrine resistant breast cancers. Non-limiting examples of such inhibitors include those that target mTOR (mammalian target of rapamycin, a serine/threonine protein kinase), PI3K (phosphoinositide 3-kinase), an AKT family serine/threonine protein kinase (members of which include Akt1, Akt2, and Akt3 in humans), and/or EGFR (epidermal growth factor receptor; HER1 in humans). The detection of gene expression may of course be in any suitable cell containing sample as described herein.

In further alternative embodiments of the disclosure, the tumor grade independent H:I ratio may be used in combination with a different molecular index for cancer prognosis (in place of one, some, or all MGI genes). Non-limiting examples of such indices include the genomic grade index (GGI) based on 97 tumor grade-associated genes (Sotiriou et al., supra) and a subset of genes within those 97 genes; the MammaPrint 70-gene signature (van 't Veer et al., supra)

and a subset of genes within those 70 genes; the Oncotype DX 21-gene recurrence score algorithm (Paik et al., supra) and a subset of genes within those 21 genes; and the Veridex 76 gene assay (Wang et al., supra) and a subset of genes within those 76 genes. In other cases, the H:I ratio may be used in combination with the expression levels of one or more genes expressed in correlation with a proliferation phenotype. In some cases, genes expressed in correlation with a proliferation phenotype are within the sets of 97, 70, 21, and 76 genes as described above. Non-limiting examples of genes expressed in correlation with a proliferation phenotype are the Ki-67 genes, STK15, Survivin, Cyclin B1, and MYBL2.

So in some embodiments, the disclosure includes assaying for the expression of the H:I ratio in combination with the expression level(s) of one or more additional genes, such as one or more selected from Ki-67, STK15, Survivin, Cyclin B1, and MYBL2. The assay method may be used to stratify ER+ subjects for prognostic value and for predictive value. As a prognostic, the stratification may be based on differential expression levels that correlate with, and so indicate, tumor aggressiveness as a non-limiting example. As a predictor, the stratification may be based on differential expression levels that correlate with, and so indicate, chemotherapy responsiveness (or sensitivity) and/or non-responsiveness (or resistance), which may also be considered as a predictor of chemotherapy benefit. As a non-limiting example, the stratification (based on expression levels) may be used to predict endocrine resistance and/or prediction of benefit from inhibitors that target endocrine resistant breast cancers. Non-limiting examples of such inhibitors include those that target mTOR (mammalian target of rapamycin, a serine/threonine protein kinase), PI3K (phosphoinositide 3-kinase), an AKT family serine/threonine protein kinase (members of which include Akt1, Akt2, and Akt3 in humans), and/or EGFR (epidermal growth factor receptor; HER1 in humans). The detection of gene expression may of course be in any suitable cell containing sample as described herein.

In an additional aspect, expression of one or more genes selected from Bub1B, CENPA, NEK2, RACGAP1, and RRM2 may be used as a prognostic factor or a predictor of clinical outcome, or to determine tumor grade in a subject with benign breast disease, such as a subject who would be diagnosed as having benign breast disease in the absence of the instant disclosure. The important role of benign breast disease is discussed by Hartmann et al. (*N. Engl. J. Med.*, 353:3 (2005)). Non-limiting examples of benign breast disease include histological findings of non-proliferative lesions, proliferative lesions without atypia, and atypical hyperplasia.

Given the observation that breast cancer occurs following a diagnosis of benign breast disease, there has been speculation that precursors of breast cancer are present in some cases of benign breast disease, such as those involving lesions with atypia or atypical hyperplasia. So this disclosure includes a method to determine tumor grade in a breast cell of a subject, such as a cell from a histological sample used to diagnose benign breast disease. The method may comprise assaying a sample of breast cells from a subject for the expression levels of Bub1B, CENPA, NEK2, RACGAP1, and RRM2, wherein said expression levels are correlated with a Grade I or Grade III tumor, or even an intermediate grade tumor. Alternatively, the method may comprise assaying for any subset of these five genes, down to any one of the genes, to determine the possible presence of tumor cells of Grade I, Grade III, or an intermediate grade. In some embodiments, the cells are from the sample used to diagnose the presence of lesions with atypia or atypical hyperplasia.

Of course the disclosure further includes the use of the MGI and the H:I ratio in a sample from subject with benign breast disease to determine whether the subject is at risk for subsequent development of breast cancer. Alternatively, the disclosure provides for the use of just the H:I ratio with such a sample to determine the risk of breast cancer development.

In a further aspect, expression of one or more genes selected from Bub1B, CENPA, NEK2, RACGAP1, and RRM2 may be used as a prognostic factor or a predictor of clinical outcome, or to determine tumor grade in a subject with ductal carcinoma in situ (or DCIS). Thus, this disclosure includes a method to determine tumor grade in a breast cell of a subject afflicted with, or suspected of having, DCIS. The cell may be one from a histological sample used to diagnose DCIS in the subject. The method may comprise assaying a sample of breast cancer cells from a subject for the expression levels of Bub1B, CENPA, NEK2, RACGAP1, and RRM2, wherein said expression levels are used as a prognostic factor or a predictor of clinical outcome, or are correlated with a Grade I or Grade III tumor, or even an intermediate grade tumor. Alternatively, the method may comprise assaying for any subset of these five genes, down to any one of the genes, as a prognostic factor or a predictor of clinical outcome, or to determine the presence of tumor cells of Grade I, Grade III, or an intermediate grade.

In another aspect, the disclosure includes compositions and methods for detecting the expression of one or more genes selected from Bub1B, CENPA, NEK2, RACGAP1, and RRM2 for use as a prognostic for local recurrence of cancer in DCIS. In some embodiments, a method based on the expression levels is advantageously used on a breast cancer cell containing sample from a subject with DCIS. As a non-limiting example, the cell may be one from a pre-operative histological sample used to diagnose cancer in the subject. For such a subject, the standard of care is surgery, with breast conserving surgery preferred over a radical mastectomy, to remove the DCIS. This is often followed by post-operative radiotherapy, optionally with endocrine therapy, such as treatment with tamoxifen, a selective estrogen receptor modulator (SERM), a selective estrogen receptor down-regulator (SERD), or an aromatase inhibitor (AI) such as letrozole, and/or with chemotherapy. But this protocol to address the possibility of cancer recurrence leads to over-treatment in many subjects that will not experience cancer recurrence and to failure, in cases of cancer recurrence.

Therefore, the disclosure includes detecting expression of all five of these genes where high MGI expression is an indicator of increased likelihood of local cancer recurrence in the subject due to failure of the breast conserving surgery and subsequent radiation therapy and/or endocrine therapy or chemotherapy. In other embodiments, such a method utilizes detection of the H:I ratio as a substitute indicator for high MGI expression. Of course, the disclosure includes a method that combines detection of high MGI and the H:I ratio as indicators of increased likelihood of local cancer recurrence following treatment for DCIS. Alternatively, the method may comprise assaying for any subset of the five MGI genes, down to any one of the genes, optionally in combination with the H:I ratio, as indicators increased likelihood of local cancer recurrence following treatment for DCIS.

The methods may further include identifying the subject as likely, or unlikely, to experience local cancer recurrence, and optionally further include adjusting treatment modalities for the subject to address the expected outcome. As a non-limiting example, determination of a low likelihood of recurrence may be used to confirm the suitability of, or to select, breast conserving surgery, optionally with reduction in post-operative therapies, such as omission of radiation and/or omission of endocrine therapy or chemotherapy. As another non-limiting example, determination of a high likelihood of recurrence may be used to confirm the suitability of, or to select, radical mastectomy with inclusion of post-operative therapies, such as radiation and/or endocrine therapy or chemotherapy.

In a yet additional aspect, the disclosure includes use of one or more genes selected from Bub1B, CENPA, NEK2, RACGAP1, and RRM2 (or all five genes) as a prognostic factor or a predictor of clinical outcome, or to determine tumor grade in a subject that is under evaluation based on the 2005 St. Gallen expert consensus on the primary therapy of early breast cancer (see Goldhirsch et al. Ann. Oncol., 6:1569-1583 (2005)). Thus, this disclosure includes a method to assess expression of one, some, or all of the MGI genes in a breast cell of a subject as part of the differential diagnosis and selection of therapy based on the expert consensus. Non-limiting examples of portions of the consensus that may be used with the disclosed methods include the algorithm for selection of adjuvant systemic therapy for early breast cancer; responsiveness or non-responsiveness to endocrine therapy or uncertain endocrine responsiveness; and nodal status. Of course inclusion of one or more aspects of the disclosure in the consensus as a whole is also contemplated. In other embodiments, the disclosed methods of molecular gene expression profiling are used to confirm classifications of low and high risk groups as well as resolve at least some intermediate risk category subjects into the low or high risk groups.

In some cases, the disclosed methods may be used to select or eliminate therapies for premenopausal women, or for postmenopausal women, diagnosed with cancer. Premenopausal women include those who are less than about 35 years of age. In these subjects, high MGI expression is an indicator of cancer recurrence. So the disclosure includes using the expression level(s) of one or more genes selected from Bub1B, CENPA, NEK2, RACGAP1, and RRM2 as a prognostic for recurrence of breast cancer, such as in cases of DCIS, in a premenopausal subject. Optionally, the H:I ratio is also assayed and used as a combination with the MGI gene(s). The method may include assaying a breast cancer cell containing sample from a subject for expression of these genes. As a non-limiting example, the cell may be one from a pre-operative histological sample used to diagnose cancer in the subject. In other cases, the method includes using expression of all five of these genes as an embodiment, where high MGI expression is an indicator of increased likelihood of cancer recurrence in the premenopausal subject.

The methods may include identifying the premenopausal subject as likely, or unlikely, to experience cancer recurrence, and optionally further include adjusting treatment modalities for the subject to address the expected outcome. As a non-limiting example, determination of a low likelihood of recurrence may be used to confirm the suitability of, or to select, breast conserving therapies, optionally with reduction in post-operative therapies like radiation and/or endocrine therapy or chemotherapy. As another non-limiting example, determination of a high likelihood of recurrence may be used to confirm the suitability of, or to select, radical treatment modalities with inclusion of post-operative therapies, such as radiation and/or endocrine therapy or chemotherapy.

In other cases, the methods may be used to aid in the selection of treatment, such as among endocrine therapy, chemotherapy, radiation therapy, or any combination thereof. In some embodiments, the disclosure includes compositions and methods for determining the expression levels of one or more of the five MGI genes, or all five of them, as a predictor of endocrine therapy effectiveness. In some cases, the predictor may be of responsiveness or non-responsiveness to an SERM, such as tamoxifen, or an SERD. This includes cases where assay of a breast cancer cell containing sample from a subject reveals a high MGI, indicating the likelihood of non-responsiveness to tamoxifen. In other cases, the predictor may be of the effectiveness of one form of endocrine therapy over another. This includes a method that determines the expression levels of one, some, or all of the MGI genes as an indicator of greater responsiveness to an aromatase inhibitor (AI) in comparison to tamoxifen or another SERM or an SERD. The method may include identification of a high MGI in the expression of one or all five genes, which indicates a likelihood of greater responsiveness to an AI over tamoxifen. Non-limiting examples of an AI include non-steroidal inhibitors such as letrozole and anastrozole and irreversible steroidal inhibitors such as exemestane.

In yet additional cases, the disclosure includes compositions and methods for the use of the expression levels of one or more of the five MGI genes, or all five of them, as a predictor of chemotherapy treatment outcome. Optionally, the H:I ratio is also assayed and used as a combination with the MGI genes. The expression levels of the genes may thus be used to predict chemo-sensitivity, such as to paclitaxel/FAC (paclitaxel followed by 5-fluorouracil, doxorubicin and cyclophosphamide) or taxol or anthracyclin therapy as a non-limiting examples. Therefore, the disclosure includes detecting expression of all five of these genes, where high MGI expression is an indicator of increased likelihood of a complete pathological response (pCR) to chemotherapy, such as post-operative (post-surgical intervention) treatment with paclitaxel/FAC as a non-limiting example. As a non-limiting example, the detecting may be of expression in a cancer cell from a pre-operative cell containing sample used to diagnose cancer in the subject. Alternatively, the method may comprise assaying for any subset of the five MGI genes, down to any one of the genes, as predicators of sensitivity or resistance to chemotherapy.

The method may further include identifying the subject as likely, or unlikely, to experience pCR, and optionally further include adjusting treatment modalities for the subject to address the expected outcome. As a non-limiting example, determination of a low likelihood of pCR may be used to confirm the suitability of, or to select, treatment with chemotherapy, such as paclitaxel/FAC. As another non-limiting example, determination of a high likelihood of pCR may be used to confirm the suitability of, or to select, omission of chemotherapy, such as omission of paclitaxel/FAC, in favor of other treatment modalities, such as radical mastectomy with inclusion of post-operative therapies, such as radiation.

The disclosure further includes compositions and methods for the use of the expression levels of one or more of the five MGI genes, or all five of them, as a predictor of a cancer's responsiveness (sensitivity) to radiation treatment. Optionally, the H:I ratio is also assayed and used as a combination with the MGI gene(s). High MGI expression may thus be used to predict a breast cancer patient to be responsive to radiation treatment, such as post-surgical intervention. Therefore, the disclosure includes detecting expression of all five of these genes, where high MGI expression is an indicator of post-operative sensitivity to radiation treatment. As a non-limiting example, the cancer cell may be one from a pre-operative histological sample used to diagnose cancer in the subject. Alternatively, the method may comprise assaying for any subset of the five MGI genes, down to any one of the genes, as predicators of responsiveness to radiation therapy.

The method may further include identifying the subject as likely, or unlikely, to be responsive to radiation therapy after surgical intervention, and optionally further include adjusting treatment modalities for the subject to address the expected outcome. As a non-limiting example, determination of a likelihood of responsiveness (sensitivity) to post-surgery radiation may be used to confirm the suitability of, or to select, radiation therapy. As another non-limiting example, determination of a low likelihood of responsiveness (sensitivity) to post-surgery radiation may be used to confirm the suitability of, or to select, omitting radiation therapy, optionally in favor of chemotherapy.

BRIEF DESCRIPTION OF THE FIGURES

FIG. 1A, illustrates the combination of the 5-gene expression pattern into a single index score (molecular grade index or MGI) via unsupervised principle component analysis. The MGI strongly correlated with tumor grade. FIG. 1B, illustrates a model-based clustering of MGI across the entire dataset, resulting in a bimodal distribution with a natural cutoff point around 0. This cutpoint correctly classified most of the grade 1 and grade 3 tumors (89% overall accuracy) and stratified grade 2 tumors into two groups (59% and 41% in the low and high MGI group, respectively). Survival probability data over 12 years from the grade 2 tumor subjects was plotted based upon MGI values of ≤0 and >0 in FIG. 1C to illustrate the prognostic capability of MGI.

FIGS. 2A-2F show a comparison of MGI and GGI for correlation with tumor grade and clinical outcome. FIGS. 2A to 2C, illustrate a comparison of the 5-gene expression pattern to GGI in the Uppsala cohort, while FIG. 2D to 2F correspond to the Stockholm cohort. FIGS. 2A and 2D are receiver operating characteristic (ROC) curve analysis of MGI and GGI for discriminating grade 1 and grade 3 tumors. FIGS. 2B to 2F show Kaplan-Meier survival curves showing probability of breast cancer-specific death according to MGI or GGI status (high vs. low).

FIGS. 3A and 3B are for all patients. FIGS. 3C and 3D correspond to the ER+ tumor grade 1 or 2 subgroup.

FIG. 4A illustrates the correlation of MGI with tumor grade. FIGS. 4B to 4D show Kaplan-Meier analyses of distant metastasis-free survival according to MGI using all patients (FIG. 4B), lymph node-negative (FIG. 4C) or lymph node-positive patients (FIG. 4D).

FIGS. 5A-D show Kaplan-Meier analyses of distant metastasis-free survival according to MGI (FIG. 5A), H:I ratio (FIG. 5B), or the three groups (low-, intermediate- and high-risk) generated by combing MGI and H:I ratio (FIG. 5C) in the MGH cohort, or the same three risk groups in the Oxford cohort (FIG. 5D).

FIG. 10A shows the results with patients that received no systemic treatment. FIG. 10B shows the results with patients that received only endocrine therapy. HR=hazard ratio from univariate Cox regression analysis, and p values are from log-rank test.

FIG. 12A shows the results with post-menopausal women (age ≥50). FIG. 12B shows the results with pre-menopausal women (age <50). HR=hazard ratio from univariate Cox regression analysis, and p values are from log-rank test.

DETAILED DESCRIPTION OF MODES OF PRACTICING THE DISCLOSURE

Definitions of Terms as Used Herein

Figure 3A:
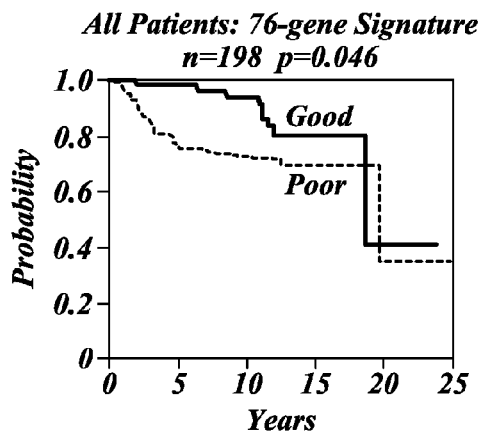
FIGS. 3A-3D show Kaplan-Meier survival curves according to the 76-gene prognostic signature or MGI in the TRANSBIG cohort.
Figure 3B:
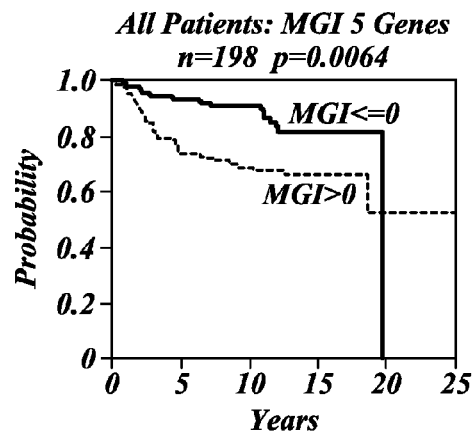
Figure 3C:
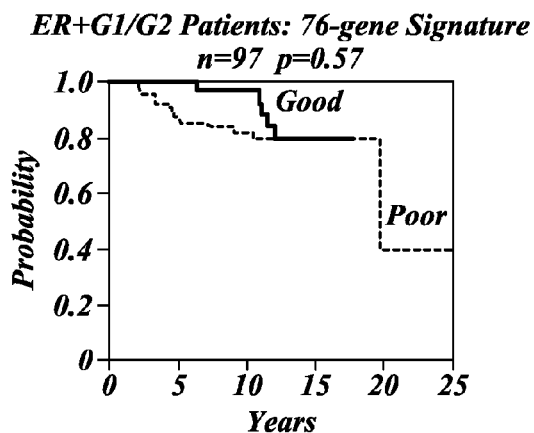
Figure 3D:
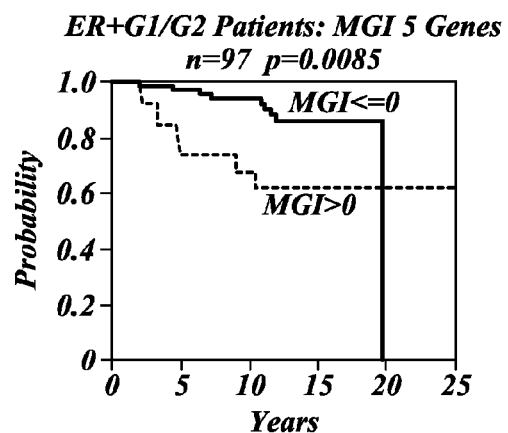

A gene expression "pattern" or "profile" or "signature" refers to the relative expression of one or more genes between two or more clinical outcomes, cancer outcomes, cancer recurrence and/or survival outcomes which is correlated with being able to distinguish between said outcomes. In some cases, the outcome is that of breast cancer.

A "gene" is a polynucleotide that encodes a discrete product, whether RNA or proteinaceous in nature. It is appreciated that more than one polynucleotide may be capable of encoding a discrete product. The term includes alleles and polymorphisms of a gene that encodes the same product, or a functionally associated (including gain, loss, or modulation of function) analog thereof, based upon chromosomal location and ability to recombine during normal mitosis.

The terms "correlate" or "correlation" or equivalents thereof refer to an association between expression of one or more genes and a physiologic state of a cell to the exclusion of one or more other state as identified by use of the methods as described herein. A gene may be expressed at a higher or a lower level and still be correlated with one or more cancer state or outcome.

A "polynucleotide" is a polymeric form of nucleotides of any length, either ribonucleotides or deoxyribonucleotides. This term refers only to the primary structure of the molecule. Thus, this term includes double- and single-stranded DNA and RNA. It also includes known types of modifications including labels known in the art, methylation, "caps", substitution of one or more of the naturally occurring nucleotides with an analog, and internucleotide modifications such as uncharged linkages (e.g., phosphorothioates, phosphorodithioates, etc.), as well as unmodified forms of the polynucleotide.

The term "amplify" is used in the broad sense to mean creating an amplification product can be made enzymatically with DNA or RNA polymerases. "Amplification," as used herein, generally refers to the process of producing multiple copies of a desired sequence, particularly those of a sample. "Multiple copies" mean at least 2 copies. A "copy" does not necessarily mean perfect sequence complementarity or identity to the template sequence.

By corresponding is meant that a nucleic acid molecule shares a substantial amount of sequence identity with another nucleic acid molecule. Substantial amount means at least 95%, usually at least 98% and more usually at least 99%, and sequence identity is determined using the BLAST algorithm, as described in Altschul et al., *J. Mol. Biol.* 215:403-410 (1990) (using the published default setting, i.e. parameters w=4, t=17). Methods for amplifying mRNA are generally known in the art, and include reverse transcription PCR (RT-PCR) and those described in U.S. patent application Ser. No. 10/062,857 (filed on Oct. 25, 2001), as well as U.S. Provisional Patent Applications 60/298,847 (filed Jun. 15, 2001) and 60/257,801 (filed Dec. 22, 2000), all of which are hereby incorporated by reference in their entireties as if fully set forth. Another method which may be used is quantitative PCR (or Q-PCR). Alternatively, RNA may be directly labeled as the corresponding cDNA by methods known in the art.

A "microarray" is a linear or two-dimensional array of preferably discrete regions, each having a defined area, formed on the surface of a solid support such as, but not limited to, glass, plastic, or synthetic membrane. The density of the discrete regions on a microarray is determined by the total numbers of immobilized polynucleotides to be detected on the surface of a single solid phase support, preferably at least about 50/cm$^2$, more preferably at least about 100/cm$^2$, even more preferably at least about 500/cm$^2$, but preferably below about 1,000/cm$^2$. Preferably, the arrays contain less than about 500, about 1000, about 1500, about 2000, about 2500, or about 3000 immobilized polynucleotides in total. As used herein, a DNA microarray is an array of oligonucleotides or polynucleotides placed on a chip or other surfaces used to hybridize to amplified or cloned polynucleotides from a sample. Since the position of each particular group of primers in the array is known, the identities of a sample polynucleotides can be determined based on their binding to a particular position in the microarray.

Because the disclosure relies upon the identification of genes that are over- or under-expressed, one embodiment of the disclosure involves determining expression by hybridization of mRNA, or an amplified or cloned version thereof, of a sample cell to a polynucleotide that is unique to a particular gene sequence. Preferred polynucleotides of this type contain at least about 20, at least about 22, at least about 24, at least about 26, at least about 28, at least about 30, or at least about 32 consecutive basepairs of a gene sequence that is not found in other gene sequences. The term "about" as used in the previous sentence refers to an increase or decrease of 1 from the stated numerical value. Even more preferred are polynucleotides of at least or about 50, at least or about 100, at least about or 150, at least or about 200, at least or about 250, at least or about 300, at least or about 350, or at least or about 400 basepairs of a gene sequence that is not found in other gene sequences. The term "about" as used in the preceding sentence refers to an increase or decrease of 10% from the stated numerical value. Such polynucleotides may also be referred to as polynucleotide probes that are capable of hybridizing to sequences of the genes, or unique portions thereof, described herein. Preferably, the sequences are those of mRNA encoded by the genes, the corresponding cDNA to such mRNAs, and/or amplified versions of such sequences. In preferred embodiments of the disclosure, the polynucleotide probes are immobilized on an array, other devices, or in individual spots that localize the probes.

In another embodiment of the disclosure, all or part of a disclosed sequence may be amplified and detected by methods such as the polymerase chain reaction (PCR) and variations thereof, such as, but not limited to, quantitative PCR (Q-PCR), reverse transcription PCR (RT-PCR), and real-time PCR, optionally real-time RT-PCR. Such methods would utilize one or two primers that are complementary to portions of a disclosed sequence, where the primers are used to prime nucleic acid synthesis. The newly synthesized nucleic acids are optionally labeled and may be detected directly or by hybridization to a polynucleotide of the disclosure. The newly synthesized nucleic acids may be contacted with polynucleotides (containing sequences) of the disclosure under conditions which allow for their hybridization.

Alternatively, and in another embodiment of the disclosure, gene expression may be determined by analysis of expressed protein in a cell sample of interest by use of one or more antibodies specific for one or more epitopes of individual gene products (proteins) in said cell sample. Such antibodies are preferably labeled to permit their easy detection after binding to the gene product.

The term "label" refers to a composition capable of producing a detectable signal indicative of the presence of the labeled molecule. Suitable labels include radioisotopes, nucleotide chromophores, enzymes, substrates, fluorescent molecules, chemiluminescent moieties, magnetic particles, bioluminescent moieties, and the like. As such, a label is any composition detectable by spectroscopic, photochemical, biochemical, immunochemical, electrical, optical or chemical means.

The term "support" refers to conventional supports such as beads, particles, dipsticks, fibers, filters, membranes and silane or silicate supports such as glass slides.

As used herein, a "cancer tissue sample" or "cancer cell sample" refers to a cell containing sample of tissue isolated from an individual afflicted with the corresponding cancer. The sample may be from material removed via a surgical procedure, such as a biopsy. Such samples are primary isolates (in contrast to cultured cells) and may be collected by any suitable means recognized in the art. In some embodiments, the "sample" may be collected by an non-invasive method, including, but not limited to, abrasion, fine needle aspiration.

A "breast tissue sample" or "breast cell sample" refers to a sample of breast tissue or fluid isolated from an individual suspected of being afflicted with, or at risk of developing, breast cancer. Such samples are primary isolates (in contrast to cultured cells) and may be collected by any non-invasive means, including, but not limited to, ductal lavage, fine needle aspiration, needle biopsy, the devices and methods described in U.S. Pat. No. 6,328,709, or any other suitable means recognized in the art. Alternatively, the "sample" may be collected by an invasive method, including, but not limited to, surgical biopsy.

"Expression" and "gene expression" include transcription and/or translation of nucleic acid material. Of course the term may also be limited, if so indicated, as referring only to the transcription of nucleic acids.

As used herein, the term "comprising" and its cognates are used in their inclusive sense; that is, equivalent to the term "including" and its corresponding cognates.

Conditions that "allow" an event to occur or conditions that are "suitable" for an event to occur, such as hybridization, strand extension, and the like, or "suitable" conditions are conditions that do not prevent such events from occurring. Thus, these conditions permit, enhance, facilitate, and/or are conducive to the event. Such conditions, known in the art and described herein, depend upon, for example, the nature of the nucleotide sequence, temperature, and buffer conditions. These conditions also depend on what event is desired, such as hybridization, cleavage, strand extension or transcription.

Sequence "mutation," as used herein, refers to any sequence alteration in the sequence of a gene disclosed herein interest in comparison to a reference sequence. A sequence mutation includes single nucleotide changes, or alterations of more than one nucleotide in a sequence, due to mechanisms such as substitution, deletion or insertion. Single nucleotide polymorphism (SNP) is also a sequence mutation as used herein. Because the present disclosure is based on the relative level of gene expression, mutations in non-coding regions of genes as disclosed herein may also be assayed in the practice of the disclosure.

"Detection" includes any means of detecting, including direct and indirect detection of gene expression and changes therein. For example, "detectably less" products may be observed directly or indirectly, and the term indicates any reduction (including the absence of detectable signal). Similarly, "detectably more" product means any increase, whether observed directly or indirectly.

Increases and decreases in expression of the disclosed sequences are defined in the following terms based upon percent or fold changes over expression in normal cells. Increases may be of 10, 20, 30, 40, 50, 60, 70, 80, 90, 100, 120, 140, 160, 180, or 200% relative to expression levels in normal cells. Alternatively, fold increases may be of 1, 1.5, 2, 2.5, 3, 3.5, 4, 4.5, 5, 5.5, 6, 6.5, 7, 7.5, 8, 8.5, 9, 9.5, or fold over expression levels in normal cells. Decreases may be of 10, 20, 30, 40, 50, 55, 60, 65, 70, 75, 80, 82, 84, 86, 88, 90, 92, 94, 96, 98, 99 or 100% relative to expression levels in normal cells.

Unless defined otherwise all technical and scientific terms used herein have the same meaning as commonly understood to one of ordinary skill in the art to which this disclosure belongs.

General

In the instant disclosure, through both data- and knowledge-driven approaches, a 5-gene tumor grade signature (MGI) was developed and implemented in a robust RT-PCR assay. One important characteristic of the MGI is that its calculation does not involve complex weighting trained on clinical outcome. Instead, it is a molecular correlate of tumor grade and derives its prognostic capacity from the latter (so-called "bottom-up" approach). The advantage of MGI over histological tumor grade is two-fold. First, like GGI, it classifies grade 2 tumors to be either grade 1-like or grade 3-like, removing most of the ambiguity of pathological tumor grading. Second, and because an RT-PCR-based assay can be standardized in the clinical laboratory, it also removes the subjectivity and inter-/intra-observer variability associated with pathological grading.

The disclosed results also show that the prognostic accuracy of MGI can be augmented by also considering the H:I ratio and vice versa, suggesting a simple algorithm that stratifies patients into three risk groups. MGI and the H:I ratio appear to represent two distinct prognostic modules in breast cancer, as suggested by the observation that the H:I ratio, but not MGI, is associated with estrogen signaling.

Beyond their prognostic capacities, MGI and the H:I ratio are also potential predictive factors for therapeutic benefit from chemotherapy and endocrine therapy, respectively. High tumor grade or mitotic index predicts benefit from chemotherapy in node-negative breast cancer patients. Similarly, the proliferation group of genes in the Recurrence Score algorithm has been shown to predict chemotherapy benefit in ER+ node-negative patients. Indeed, high MGI predicts complete pathological response in ER+ breast cancer patients treated with preoperative paclitaxel followed by 5-fluorouracil, doxorubicin, and cyclophosphamide.

Two recent studies of the H:I ratio have demonstrated its potential as a novel biomarker of endocrine responsiveness beyond estrogen and progesterone receptors. In a study of recurrent breast cancer, low H:I was strongly associated with response to first-line tamoxifen therapy. Similarly, in an analysis of tumor samples from a prospective randomized clinical trial comparing 2 years vs. 5 years of tamoxifen therapy, low HOXB13 or low H:I ratio significantly predicted benefit from prolonged tamoxifen therapy. These results are consistent with the observation that estrogen negatively regulates HOXB13 and positively regulates IL17BR expression. Thus, in ER+ tumors, a high HOXB13 or H:I index can be considered as a marker of dysfunctional estrogen signaling.

The dual roles of MGI and the H:I ratio are especially relevant in the context of the latest (2005) St. Gallen consensus guidelines for treatment selection for early stage breast cancer. The St. Gallen guidelines classify ER+ node-negative breast cancer patients into low and intermediate risk groups, with the majority falling into the latter. An important treatment decision is whether to withhold chemotherapy for some of the patients in the intermediate-risk group, a question targeted by two new prospective clinical trials. In the Table 1 cohort described herein, applying the St. Gallen guidelines resulted in the classification of 86% the patients into the intermediate risk group, which could be re-classified as low (43%), intermediate (26%) or high (31%) risk using MGI and the H:I ratio.

The excellent disease-free survival probability of the low risk patients suggests that they could be potentially spared from toxic chemotherapy without compromising their prognosis, whereas more intense chemotherapy regimens or new therapeutic agents should be added to the high-risk group. Therefore, risk stratification based on MGI and the H:I ratio and their respective predictive capacities could be added to existing guidelines to better balance the risk-benefit ratio of current treatment modalities.

Therefore, this disclosure includes a validated MGI as a powerful prognostic factor in ER+ breast cancer. Furthermore, MGI and the H:I ratio can be combined to provide more accurate prognostic information than either alone. The identification of a subset of patients with very poor outcome using these two biomarkers facilitates clinical trial designs to target those cancers with both high MGI and high H:I ratio.

MGI

The genes disclosed as expressed in correlation with particular tumor grades provide the ability to focus gene expression analysis to only those genes that contribute to the ability to identify a subject as likely to have a particular prognosis, or clinical outcome, relative to another. The expression of other genes in a cancer cell would be relatively unable to provide information concerning, and thus assist in these discriminations.

To determine the expression levels of genes in the practice of the present disclosure, any method known in the art may be utilized. In some embodiments, expression based on detection of RNA which hybridizes to the genes identified and disclosed herein is used. This is readily performed by any RNA detection or amplification+detection method known or recognized as equivalent in the art such as, but not limited to, reverse transcription-PCR, the methods disclosed in U.S. patent application Ser. No. 10/062,857 (filed on Oct. 25, 2001) as well as U.S. Provisional Patent Application 60/298,847 (filed Jun. 15, 2001) and 60/257,801 (filed Dec. 22, 2000), and methods to detect the presence, or absence, of RNA stabilizing or destabilizing sequences.

Alternatively, expression based on detection of DNA status may be used. Detection of the DNA of an identified gene as methylated or deleted may be used for genes that have decreased expression. This may be readily performed by PCR based methods known in the art, including, but not limited to, Q-PCR. Conversely, detection of the DNA of an identified gene as amplified may be used for genes that have increased expression in correlation with a particular breast cancer outcome. This may be readily performed by PCR based, fluorescent in situ hybridization (FISH) and chromosome in situ hybridization (CISH) methods known in the art.

Expression based on detection of a presence, increase, or decrease in protein levels or activity may also be used. Detection may be performed by any immunohistochemistry (IHC) based, blood based (especially for secreted proteins), antibody (including autoantibodies against the protein) based, exfoliate cell (from the cancer) based, mass spectroscopy based, and image (including used of labeled ligand) based method known in the art and recognized as appropriate for the detection of the protein. Antibody and image based methods are additionally useful for the localization of tumors after determination of cancer by use of cells obtained by a non-invasive procedure (such as ductal lavage or fine needle aspiration), where the source of the cancerous cells is not known. A labeled antibody or ligand may be used to localize the carcinoma(s) within a patient.

One embodiment using a nucleic acid based assay to determine expression is by immobilization of one or more sequences of the genes identified herein on a solid support, including, but not limited to, a solid substrate as an array or to beads or bead based technology as known in the art. Alternatively, solution based expression assays known in the art may also be used.

The immobilized gene(s) may be in the form of polynucleotides that are unique or otherwise specific to the gene(s) such that the polynucleotide would be capable of hybridizing to a DNA or RNA corresponding to the gene(s). These polynucleotides may be the full length of the gene(s) or be short sequences of the genes (up to one nucleotide shorter than the full length sequence known in the art by deletion from the 5' or 3' end of the sequence) that are optionally minimally interrupted (such as by mismatches or inserted non-complementary basepairs) such that hybridization with a DNA or RNA corresponding to the gene(s) is not affected. In some cases, the polynucleotides used are from the 3' end of the gene, such as within about 350, about 300, about 250, about 200, about 150, about 100, or about 50 nucleotides from the polyadenylation signal or polyadenylation site of a gene or expressed sequence. Polynucleotides containing mutations relative to the sequences of the disclosed genes may also be used so long as the presence of the mutations still allows hybridization to produce a detectable signal.

The immobilized gene(s) may be used to determine the state of nucleic acid samples prepared from sample cancer, or breast, cell(s) for which the outcome of the sample's subject (e.g. patient from whom the sample is obtained) is not known or for confirmation of an outcome that is already assigned to the sample's subject. Without limiting the disclosure, such a cell may be from a patient with ER+ breast cancer. The immobilized polynucleotide(s) need only be sufficient to specifically hybridize to the corresponding nucleic acid molecules derived from the sample under suitable conditions.

The disclosure is based in part upon the discovery of a gene expression based prognostic factor and predictor of clinical outcome and tumor grade, such as that which utilize cancer samples from FFPE tissues, frozen samples or fresh samples. The expression levels of these genes correlate with tumor grade and clinical outcomes as described herein as well as determining prognosis for a subject. The identified genes have roles in the cell cycle and reported peak expression as follows:

| Gene | Peak of Expression | Role in Cell Cycle |
| --- | --- | --- |
| BUB1B | G2/M | mitotic spindle assembly checkpoint |
| CENPA | G2/M | centromere assembly |
| NEK2 | G2/M | centrosome duplication |
| RACGAP1 | Not Determined | Initiation of cytokinesis |
| RRM2 | S | DNA replication |

The sequences of these genes have been previously reported and characterized in the field. For example, and on Sep. 6, 2007, the human BUB1B (also known as p21 protein-activated kinase 6 or PAK6) gene was identified by Unigene Hs.631699 and was characterized by 273 corresponding sequences. On Mar. 6, 2010, the same gene information was identified by UniGene Hs.513645 and characterized as corresponding to chromosome 15 at position 15q14 and as supported by 23 mRNA sequences and 549 EST sequences.

Also on Sep. 6, 2007, the human CENPA gene was identified by Hs.1594 (with 129 corresponding sequences). On Mar. 6, 2010, the same gene information was characterized as corresponding to chromosome 2 at 2p24-p21 and as supported by 10 mRNA sequences and 119 EST sequences.

Also on Sep. 6, 2007, the human NEK2 gene was identified by Hs.153704 (with 221 corresponding sequences). On Mar. 6, 2010, the same gene information was characterized as corresponding to chromosome 1 at 1q32.2-q41 and as supported by 17 mRNA sequences and 205 EST sequences.

Also on Sep. 6, 2007, the human RACGAP1 gene was identified by Hs.696319 (with 349 corresponding sequences). On Mar. 6, 2010, the same gene information was identified by UniGene Hs.505469 and characterized as corresponding to chromosome 12 at position 12q13.12 and as supported by 15 mRNA sequences and 398 EST sequences.

Also on Sep. 6, 2007, the human RRM2 gene was identified by Hs.226390 (with 1348 corresponding sequences). On Mar. 6, 2010, the same gene information was characterized as corresponding to chromosome 2 at 2p25-p24 and as supported by 25 mRNA sequences and 1328 EST sequences.

The mRNA and EST sequences corresponding to each of the above Unigene identifiers are hereby incorporated by reference as if fully set forth and may be used in the practice of the disclosure by the skilled person as deemed appropriate.

Two representative BUB1B mRNA sequences identified by Unigene Hs.513645 are disclosed in the Sequence Listing; two representative CENPA mRNA sequences identified by Hs.1594 are disclosed in the Sequence Listing; two representative NEK2 mRNA sequences identified by Hs.153704 are disclosed in the Sequence Listing; two representative RACGAP1 mRNA sequences identified by Hs.505469 are disclosed in the Sequence Listing; and two representative RRM2 mRNA sequences identified by Hs.226390 are disclosed in the Sequence Listing. The sequences disclosed in the Listing are non-limiting for the practice of the disclosed invention but are provided as evidence of the substantial knowledge in the field regarding sequences that are the disclosed genes. Additionally, the skilled person is fully capable of aligning any two or more of the known expressed sequences for each of these genes to identify an area of identity or conserved changes as a region that uniquely identifies each of these genes in comparison to other genes. Furthermore, the skilled person is fully capable of aligning any two or more of the known expressed sequences for each of these genes to identify an area unique to one or more of the of the expressed sequences as a region that uniquely identifies one known expressed sequence relative to at least one other expressed sequence. As a non-limiting example, a unique region may be in a variant of the expressed sequence for one of the known genes such that the region may be used to identify expression of the variant.

The sequences of the same genes have also been identified and characterized from other animal species. Thus the skilled person in the field is clearly aware of how to identify the disclosed genes relative to other animal genes. The skilled person may also optionally compare the known sequences of the disclosed genes from different animal sources to identify conserved regions and sequences unique to these genes relative to other genes.

Similarly, the use of STK15, Survivin, Cyclin B1, and MYBL2 as described herein is supported by the previous reports regarding these genes and representative sequences of each of these genes known to the skilled person.

As will be appreciated by those skilled in the art, some of the corresponding sequences noted above include 3' poly A (or poly T on the complementary strand) stretches that do not contribute to the uniqueness of the disclosed sequences. The disclosure may thus be practiced with sequences lacking the 3' poly A (or poly T) stretches. The uniqueness of the disclosed sequences refers to the portions or entireties of the sequences which are found only in the disclosed gene's nucleic acids, including unique sequences found at the 3' untranslated portion of the genes. Preferred unique sequences for the practice of the disclosure are those which contribute to the consensus sequences for each of the three sets such that the unique sequences will be useful in detecting expression in a variety of individuals rather than being specific for a polymorphism present in some individuals. Alternatively, sequences unique to an individual or a sub-population may be used. The preferred unique sequences are preferably of the lengths of polynucleotides of the disclosure as discussed herein.

To determine the (increased or decreased) expression levels of the above described sequences in the practice of the disclosure, any method known in the art may be utilized. In one embodiment of the disclosure, expression based on detection of RNA which hybridizes to polynucleotides containing the above described sequences is used. This is readily performed by any RNA detection or amplification+ detection method known or recognized as equivalent in the art such as, but not limited to, reverse transcription-PCR (optionally real-time PCR), the methods disclosed in U.S. patent application Ser. No. 10/062,857 entitled "Nucleic Acid Amplification" filed on Oct. 25, 2001 as well as U.S. Provisional Patent Application 60/298,847 (filed Jun. 15, 2001) and 60/257,801 (filed Dec. 22, 2000), the methods disclosed in U.S. Pat. No. 6,291,170, and quantitative PCR. Methods to identify increased RNA stability (resulting in an observation of increased expression) or decreased RNA stability (resulting in an observation of decreased expression) may also be used. These methods include the detection of sequences that increase or decrease the stability of mRNAs containing the genes' sequences. These methods also include the detection of increased mRNA degradation.

In some embodiments of the disclosure, polynucleotides having sequences present in the 3' untranslated and/or non-coding regions of the above disclosed sequences are used to detect expression levels of the gene sequences in cancer, or breast, cells. Such polynucleotides may optionally contain sequences found in the 3' portions of the coding regions of the above disclosed sequences. Polynucleotides containing a combination of sequences from the coding and 3' non-coding regions preferably have the sequences arranged contiguously, with no intervening heterologous sequences.

Alternatively, the disclosure may be practiced with poly-nucleotides having sequences present in the 5' untranslated and/or non-coding regions of the gene sequences in cancer, or breast, cells to detect their levels of expression. Such polynucleotides may optionally contain sequences found in the 5' portions of the coding regions. Polynucleotides containing a combination of sequences from the coding and 5' non-coding regions preferably have the sequences arranged contiguously, with no intervening heterologous sequences. The disclosure may also be practiced with sequences present in the coding regions of the disclosed gene sequences.

Non-limiting polynucleotides contain sequences from 3' or 5' untranslated and/or non-coding regions of at least about 20, at least about 22, at least about 24, at least about 26, at least about 28, at least about 30, at least about 32, at least about 34, at least about 36, at least about 38, at least about 40, at least about 42, at least about 44, or at least about 46 consecutive nucleotides. The term "about" as used in the previous sentence refers to an increase or decrease of 1 from the stated numerical value. Even more preferred are poly-nucleotides containing sequences of at least or about 50, at least or about 100, at least about or 150, at least or about 200, at least or about 250, at least or about 300, at least or about 350, or at least or about 400 consecutive nucleotides. The term "about" as used in the preceding sentence refers to an increase or decrease of 10% from the stated numerical value.

Sequences from the 3' or 5' end of the above described coding regions as found in polynucleotides of the disclosure are of the same lengths as those described above, except that they would naturally be limited by the length of the coding region. The 3' end of a coding region may include sequences up to the 3' half of the coding region. Conversely, the 5' end of a coding region may include sequences up the 5' half of the coding region. Of course the above described sequences, or the coding regions and polynucleotides containing portions thereof, may be used in their entireties.

Polynucleotides combining the sequences from a 3' untranslated and/or non-coding region and the associated 3' end of the coding region may be at least or about 100, at least about or 150, at least or about 200, at least or about 250, at least or about 300, at least or about 350, or at least or about 400 consecutive nucleotides. Preferably, the polynucleotides used are from the 3' end of the gene, such as within about 350, about 300, about 250, about 200, about 150, about 100, or about 50 nucleotides from the polyadenylation signal or polyadenylation site of a gene or expressed sequence. Polynucleotides containing mutations relative to the sequences of the disclosed genes may also be used so long as the presence of the mutations still allows hybridization to produce a detectable signal.

In another embodiment of the disclosure, polynucleotides containing deletions of nucleotides from the 5' and/or 3' end of the above disclosed sequences may be used. The deletions are preferably of 1-5, 5-10, 10-15, 15-20, 20-25, 25-30, 30-35, 35-40, 40-45, 45-50, 50-60, 60-70, 70-80, 80-90, 90-100, 100-125, 125-150, 150-175, or 175-200 nucleotides from the 5' and/or 3' end, although the extent of the deletions would naturally be limited by the length of the disclosed sequences and the need to be able to use the polynucleotides for the detection of expression levels.

Other polynucleotides of the disclosure from the 3' end of the above disclosed sequences include those of primers and optional probes for quantitative PCR. In some embodiments, the primers and probes are those which amplify a region less than about 350, less than about 300, less than about 250, less than about 200, less than about 150, less than about 100, or less than about 50 nucleotides from the from the polyadenylation signal or polyadenylation site of a gene or expressed sequence.

In yet other embodiments of the disclosure, polynucleotides containing portions of the above disclosed sequences including the 3' end may be used. Such polynucleotides would contain at least or about 50, at least or about 100, at least about or 150, at least or about 200, at least or about 250, at least or about 300, at least or about 350, or at least or about 400 consecutive nucleotides from the 3' end of the disclosed sequences.

The disclosure also includes polynucleotides used to detect gene expression in breast cells. The polynucleotides may comprise a shorter polynucleotide consisting of sequences found in the above genes in combination with heterologous sequences not naturally found in combination with the sequences. Non-limiting examples include short sequences from cloning vectors or present in restriction fragments used to prepare labeled probes or primers as described herein.

Methods

As described herein, the disclosure includes the identity of genes, the expression of which can be used to provide prognostic information related to cancer. In particular, the expression levels of these genes may be used in relation to breast cancer. In some methods, the gene expression profile correlates with (and so are able to discriminate between) patients with good or poor cancer recurrence and/or survival outcomes. In other embodiments, the disclosure includes a method to compare gene expression in a sample of cancer cells from a patient to the gene expression profile to determine the likely clinical or treatment outcome for the patient, or natural biological result, in the absence of intervention.

These embodiments of the disclosure may be advantageously used to meet an important unmet diagnostic need for the ability to predict whether a patient will likely benefit from a given treatment type or whether a patient will be better off with another type of treatment. For example, a low H:I ratio value is strongly associated with response to first-line tamoxifen therapy. And an analysis of tumor samples from a prospective randomized clinical trial comparing 2 years vs. 5 years of tamoxifen therapy indicates that low HOXB13 or low HOXB13:IL17BR significantly predicts benefit from prolonged tamoxifen therapy.

Figure 8:
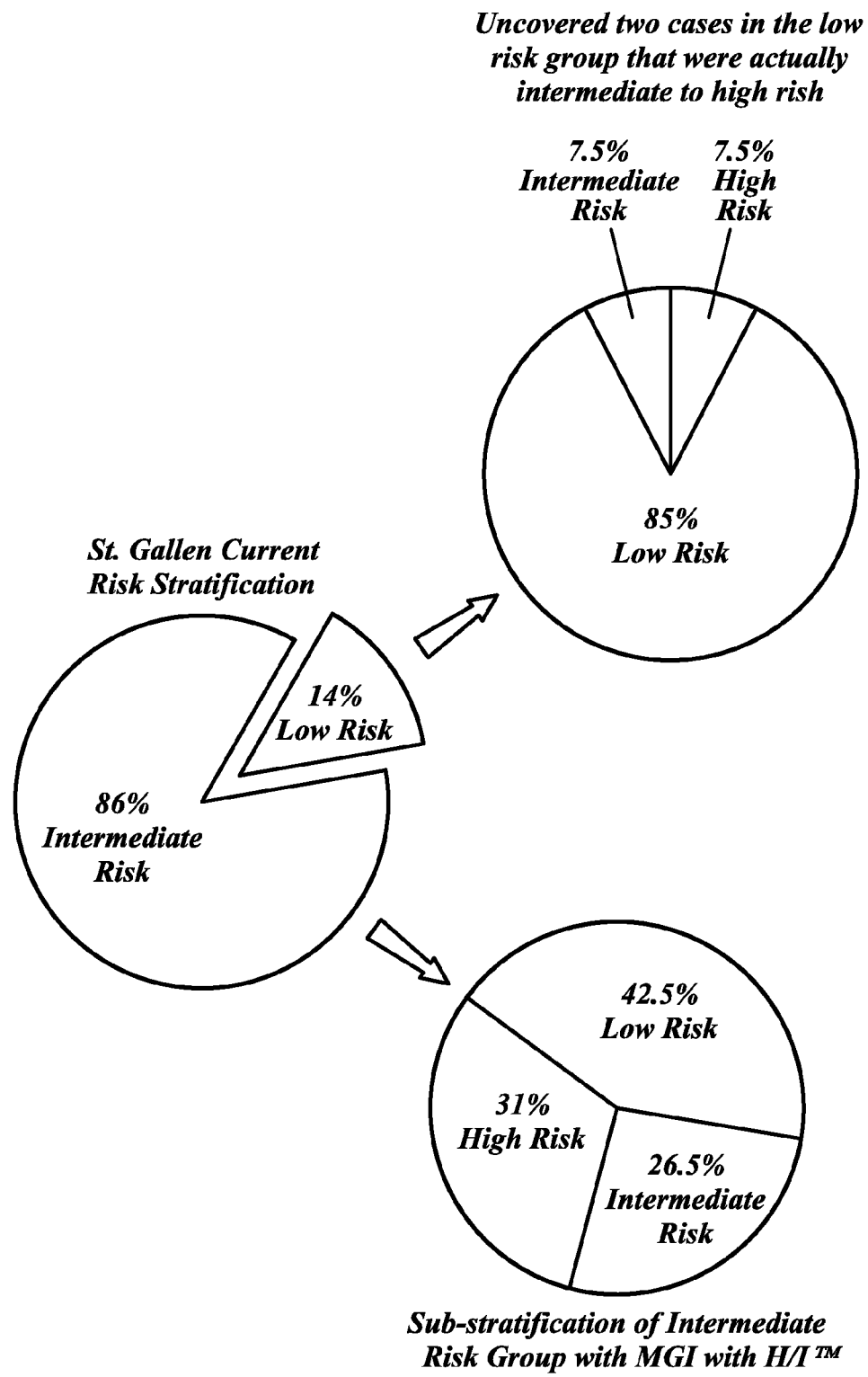
FIG. 8 illustrates application of the MGI to more accurately identify the intermediate and low risk populations under St. Gallen protocols into high, intermediate, and low risk populations.

Similarly, the ability of the MGI to predict the presence of grade I versus grade III tumors allows the clinician in the relevant field to select therapy appropriate to cancers of these two grades. The MGI not only confirms grade I and grade III classifications made by other means, but it can, in combination with the H:I ratio, more accurately classify tumors as low, intermediate, or high risk that have been incorrectly classified by other methods. This is illustrated in FIG. 8, where stratification based on 2005 St. Gallen protocol is significantly corrected by the use of the disclosed MGI and H:I ratio So the disclosure includes a method to identify a patient, from a population of patients with cancer cells, as belonging to a subpopulation of patients with a better prognosis or a subpopulation with a poor prognosis. The subpopulation with a better prognosis is similar to subjects identified as having a Grade I tumor compared to a subpopulation of patients with a poorer prognosis, similar to subjects identified as having a Grade III tumor. Of course the disclosed methods are not necessarily perfect in application, and it is possible that a given patient will be identified as having an "intermediate" tumor grade between that of Grades I and III. In which case, the skilled practitioner would treat the subject accordingly.

But the disclosure nevertheless provides a non-subjective means for the identification of patients with tumors of Grade I, intermediate, or Grade III, which identification can be used to a patient's benefit by the skilled practitioner. Importantly, the disclosed methods can classify tumors of "intermediate" grade by other methods into Grade I or Grade III status. This provides an enormous benefit to the corresponding patient subpopulation, which would otherwise have been treated as having "intermediate" grade tumors. So in some embodiments, a method of reducing the number of "intermediate" grade classification is provided by use of the disclosed 5-gene MGI.

Thus the disclosure includes a method of determining prognosis and/or survival outcome by assaying for the expression patterns disclosed herein. So where subjective interpretation may have been previously used to determine the prognosis and/or treatment of cancer patients, this disclosure provides objective gene expression patterns, which may used alone or in combination with subjective criteria to provide a more accurate assessment of patient outcomes, including survival and the recurrence of cancer. In some cases, the assaying includes detecting the expression level of Bub1B, wherein the expression level is correlated with a Grade I or Grade III tumor.

The disclosed genes are identified as correlated with tumor grade and clinical outcomes such that the levels of their expression are relevant to a determination of the treatment protocols of a patient. So in some embodiments, the disclosure provides a method to determine therapeutic treatment for a cancer patient by determining prognosis for said patient by assaying a sample of cancer cells from said patient for the expression levels described herein to determine the tumor grade, and selecting a treatment for a patient with a tumor of such grade. In some cases, the assaying includes detecting the expression level of Bub1B, wherein the expression level is correlated with a Grade I or Grade III tumor.

In one set of embodiments, a method of the disclosure may include assaying a sample of cancer cells from a cancer afflicted subject for the expression level of Bub1B wherein the expression level classifies the cancer as corresponding to a Grade I or Grade III tumor, or identifies the subject as having a prognosis of likely cancer recurrence, or predicts the responsiveness of the subject to treatment with endocrine therapy, chemotherapy, or radiation therapy. The assaying may include measuring or detecting or determining the expression level of the gene in any suitable means described herein or known to the skilled person. In many cases, the cancer is breast cancer, and the subject is a human patient. Additionally, the cancer cells may be those of a tumor and/or from a node negative (lymph nodes negative for cancer) or node positive (lymph nodes positive for cancer) subject.

Of course the method may be practiced along with assaying for the expression of one or more of the other four genes of the MGI, wherein the expression levels of the genes used in combination are used to classify, identify, or predict as provided by the method. The requisite level of expression level may be that which is identified by the methods described herein for the genes used. Additionally, the assaying may include preparing RNA from the sample, optionally for use in PCR (polymerase chain reaction) or other analytical methodology as described herein. The PCR methodology is optionally RT-PCR (reverse transcription-PCR) or quantitative PCR, such as real-time RT-PCR. Alternatively, the assaying may be conducted by use of an array, such as a microarray as known in the relevant field. Optionally, the sample of cancer cells is dissected from tissue removed or obtained from said subject. As described herein, a variety of sample types may be used, including a formalin fixed paraffin embedded (FFPE) sample as a non-limiting example. And as described herein, the method may include assaying or determining the H:I ratio (ratio of HoxB13 and IL17BR expression levels) in the sample as disclosed herein.

By way of non-limiting example, all five genes of the MGI may be assayed and used to detect expression levels that correspond to a value that is "high risk" (which is above the cutoff) for MGI, or to detect expression levels that correspond to a value that is "low risk" (which is at or below the cutoff) for MGI, as disclosed herein. In some cases, the MGI cutoff threshold may be 0 (zero), such as where the measurements of expression levels are standardized to 0 (zero) with a standard deviation of 1. In alternative embodiments, the cutoff may be at or about 0.05, at or about 0.10, at or about 0.15, at or about 0.20, at or about 0.25, at or about −0.05, at or about −0.10, at or about −0.15, at or about −0.20, at or about −0.25, at or about −0.30, at or about −0.35, at or about −0.40, at or about −0.45, at or about −0.50, at or about −0.55, at or about −0.60, at or about −0.65, at or about −0.70, at or about −0.75, at or about −0.80, at or about −0.85, at or about −0.90, at or about −0.95, at or about −1.0, at or about −1.1, at or about −1.2, at or about −1.3, at or about −1.4, at or about −1.5, at or about −1.6, at or about −1.7, at or about −1.8, at or about −1.9, at or about −2.0 or lower. With respect to the H:I ratio, its determination maybe made as described in Ma et al., *Cancer Cell,* 5:607-16 (2004) and Ma et al. (2006) as referenced herein. For example, a value of 0.06 may be used to determine whether a sample has a "high risk" (>0.06) or "low risk" (≤0.06) H:I ratio.

So using a threshold, or cutoff, of 0 (zero) as a non-limiting example for MGI with all five genes, the disclosed methods provide two possible assay outcomes for a given sample: "high risk MGI" corresponding to a value above 0 (zero) and "low risk MGI" corresponding to a value ≤0. A "high risk MGI" is indicative of a "high risk" cancer, including breast cancer, that is analogous to that of a Grade III tumor as defined by methodologies and standards known in the field. A "low risk MGI" is indicative of a "low risk" cancer, including breast cancer, that is analogous to that of a Grade I tumor as defined by methodologies and standards known in the field.

Figure 4A:
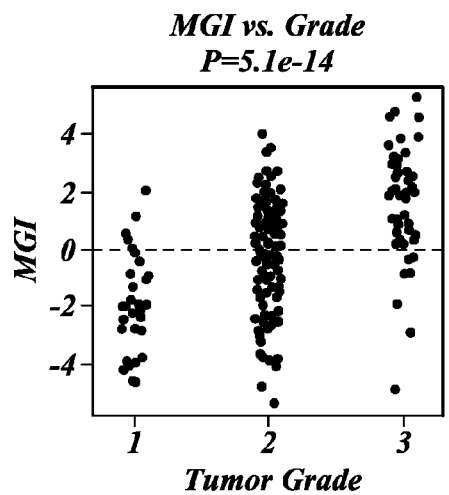
FIGS. 4A-4D show MGI determined by the RT-PCR TaqMan™ assay in the MGH cohort.
Figure 4B:
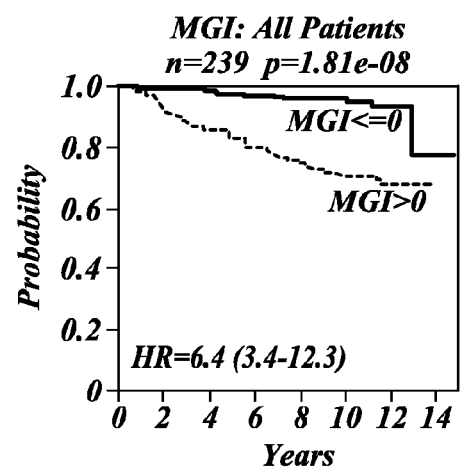

The stratification, or classification, of cancers into two groups is shown in FIG. 1C and in FIG. 4B, where the level of risk identified by a "high risk MGI" is indicative of an increased likelihood of cancer recurrence, such as cancer metastases or distal recurrence of cancer, including recurrence of breast cancer. In many embodiments, this risk of recurrence is present regardless of treatment with or without tamoxifen or other endocrine therapies. In embodiments disclosed herein, the recurrence may be local recurrence of DCIS. The level of risk identified by a "low risk MGI" is indicative of reduced likelihood of cancer recurrence, including reduced likelihood of breast cancer recurrence. In many embodiments, the reduced risk of recurrence is present regardless of treatment with or without tamoxifen. The risk of recurrence, or likelihood of no recurrence, may be considered as risk over time, such as a period of about 1, about 2, about 3, about 4, about 5, about 6, about 7, about 8, about 9, about 10, about 11, about 12 or more years. Therefore, the risk assessment provided by MGI may be used as a prognostic indicator of cancer recurrence and/or survival outcome for a subject.

Figure 9:
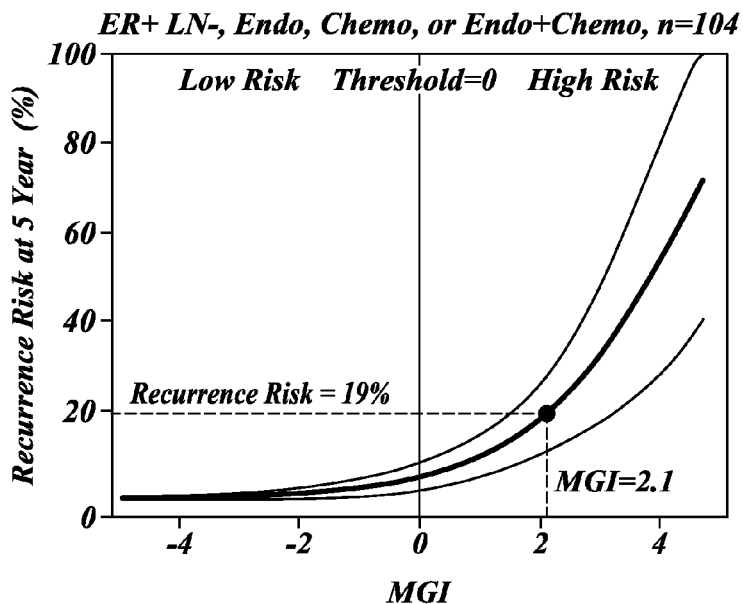
FIG. 9 illustrates a hypothetical result of an MGI value of 2.1 and its correlation with a 19% risk of cancer recurrence within 5 years.

The disclosure further includes the determination of a recurrence risk over time based upon the MGI value relative to the risk of recurrence determined by the methodologies described herein. FIG. 9 illustrates a non-limiting example of an MGI value of 2.1 and its indication of a 19% risk of cancer recurrence within 5 years. The figure further illustrates that the risk of recurrence is related to the value of the MGI, and that the selection of 0 (zero) as the threshold or cutoff value is non-limiting because other values may also be used.

Where combined with the H:I ratio, the four possible assay outcomes are as follows:

1) "high risk MGI" and "high risk H:I" which may be considered "high risk" like a "high risk MGI" alone;
2) "high risk MGI" and "low risk H:I" which may be considered as analogous to an "intermediate risk" of cancer recurrence;
3) "low risk MGI" and "high risk H:I" which may be considered "low risk" like a "low risk MGI" alone; and
4) "low risk MGI" and "low risk H:I" which may be considered "low risk" like a "low risk MGI" alone.

Figure 5E:
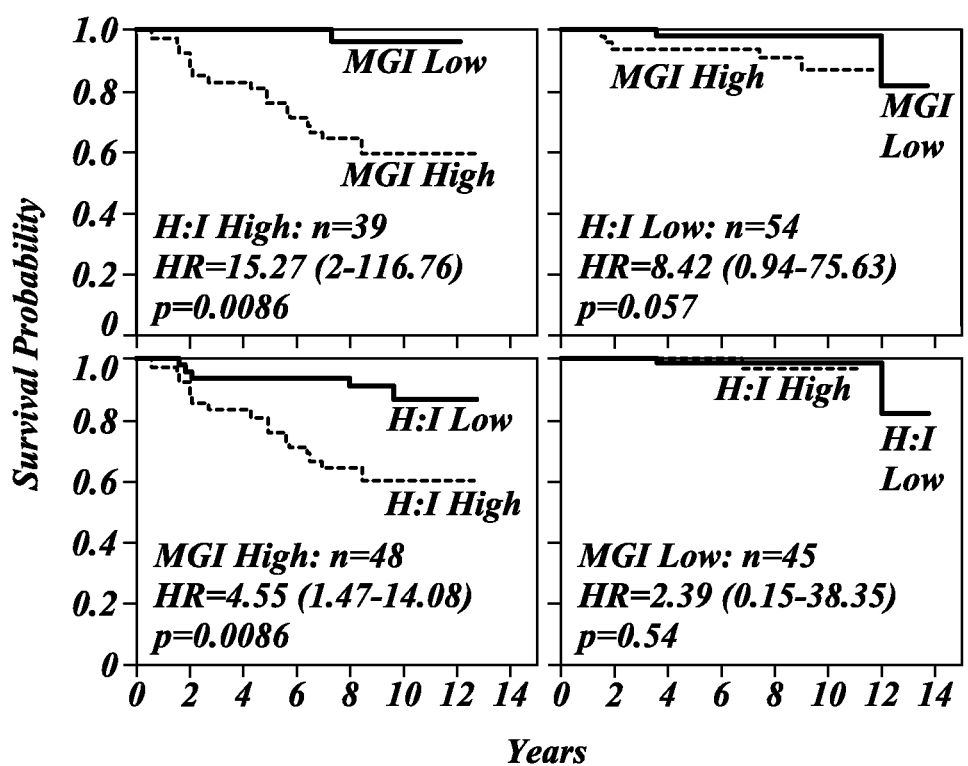
FIG. 5E illustrates the interaction between MGI and the H:I ratio in the Table 1 cohort. The node-negative endocrine therapy- or endocrine therapy+ chemotherapy-treated patients (n=93) of the cohort was analyzed for interaction between MGI and the H:I ratio. MGI was most robust in predicting distant metastasis in high HOXB13:IL17BR patients, and similarly, the H:I ratio was most robust in high MGI patients.

The combination of MGI and H:I thus identifies 3 different subtypes that have been observed to differ in their tumor biology and are associated with different patient outcomes. For example, an intermediate risk may be used to treat the patient with this tumor with endocrine therapy (such as tamoxifen as a non-limiting example) based on the prediction that the patient will benefit therefrom. In contrast, a patient with "high risk MGI" and "high risk H:I" is unlikely to benefit from endocrine mono-therapy. Therefore, the assessment does not represent a simple continuum of risk. This helps a skilled clinician because the assessment identifies the underlying biology which is helpful with respect to treatment choices. To make a choice of therapies, a clinician may determine that when patient is high risk (i.e. high/high) then knowing that this patient is unlikely to benefit from endocrine mono-therapy is a vital piece of information. This allows the clinician to consider and/or select or apply a more aggressive chemotherapy or suggest that this patient enroll in a trial that targets tumors that are resistant to endocrine mono-therapy. FIGS. 5C and 5D, demonstrate an application of these three risk groups in different populations of patients. Alternatively, these possible combinations of MGI and H:I determinations are used as indicators in the same manner as the use of MGI alone described above.

Figure 10A:
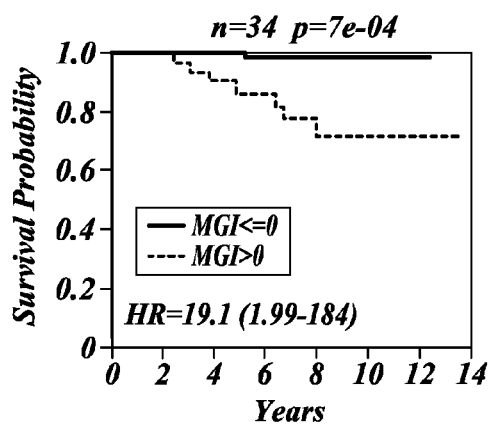
FIGS. 10A-10B show Kaplan-Meier curve analyses of patient stratification by MGI according to clinical treatment or lack thereof.
Figure 10B:
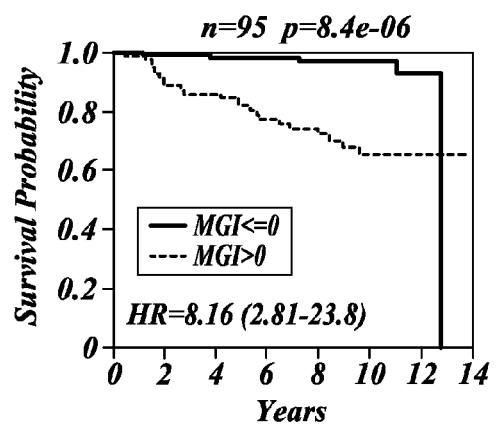

The ability of MGI to indicate risk of recurrence despite treatment with tamoxifen is also shown in FIGS. 10A and B, where "high risk" MGI is used an indicator of recurrence despite treatment with tamoxifen as monotherapy. Of course a combination of MGI and H:I determinations may also be used to the same effect. The disclosure further includes using MGI alone, H:I alone, or a combination of MGI and H:I to predict responsiveness to an inhibitor that targets endocrine resistant cancers as described herein. The possible indication of non-responsive to endocrine therapy and responsiveness to the disclosed inhibitors may be combined with another aspect of the disclosure which is a method to select therapies based upon the prognostic and predictive indications determined by the disclosed methods. So with "high risk" MGI, "high risk" H:I, or a combination of MGI and H:I determinations as described above, embodiments of the disclosure include methods further including selecting, and optionally treating, the subject with the inhibitor to improve responsiveness to tamoxifen or another form of endocrine therapy. In some cases, the method further includes treatment with tamoxifen or other form of endocrine therapy. The above description related to responsiveness to an inhibitor that targets endocrine resistant cancers may also be applied in cases of assaying for the H:I ratio alone as described herein.

The disclosure further includes assaying for a "high risk" MGI, optionally with an H:I determination, as an indicator of non-responsiveness to other forms of endocrine therapy, such as treatment with an SERM, an SERD, or an AI. Of course the disclosure also includes the determination of a "low risk" MGI, optionally with an H:I determination, as an indicator of responsiveness to tamoxifen and other SERMs as well as an SERD or an AI.

These possible predictions relative to endocrine therapy may also be used in relation to methods to select therapies as disclosed herein. For example, a method may include not selecting endocrine therapy in favor of other therapies such as chemotherapy and/or radiation therapy where lack of response is predicted. Conversely, the method may include selection of endocrine therapy where responsiveness is predicted.

In further embodiments, the assay for a "high risk" MGI, "high risk" H:I, or a combination of MGI and H:I values, may also be used as an indicator of relative responsiveness within endocrine therapy, such as better responsiveness to treatment with an AI relative to an SERM. As a non-limiting example, a "high risk" MGI value may be used as an indicator of responsiveness to an AI, such as letrozole, relative to tamoxifen. Of course the disclosure further includes a method of selecting treatment with an AI based upon such a prediction.

Figure 11:
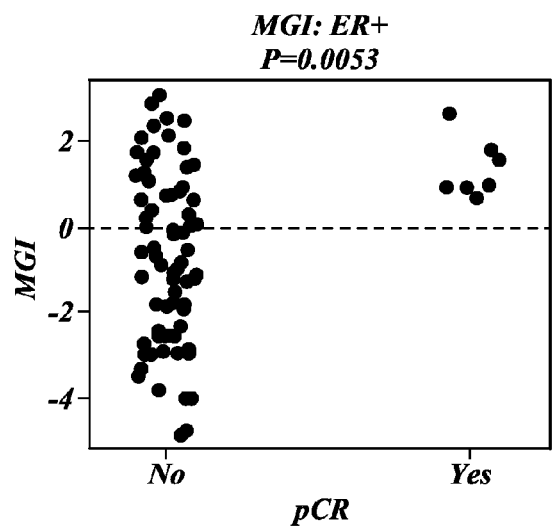
FIG. 11 shows the predictive ability of MGI for sensitivity to chemotherapy.

Beyond endocrine therapy, MGI alone, H:I alone, or a combination of MGI and H:I determinations may also be used to indicate non-responsiveness to chemotherapy. As shown in FIG. 11, "high risk" MGI is predictive of resistance to chemotherapy with paclitaxel, 5-fluorouracil, doxorubicin and cyclophosphamide as a non-limiting example. Of course the disclosure further includes a method of not selecting chemotherapy as the sole therapy in favor of other treatment modalities, such as radiation as a non-limiting example.

In addition to endocrine therapy and chemotherapy, the disclosure includes determination of MGI alone, H:I alone, or a combination of MGI and H:I determinations as a predictor of a cancer's responsiveness (sensitivity) to radiation treatment. A "high risk" MGI may be used to predict a cancer patient to be responsive to radiation treatment, such as after surgical intervention. The method may further include identifying the subject as likely, or unlikely, to be responsive to radiation therapy after surgical intervention. Of course the disclosure further includes a method of selecting radiation therapy based upon prediction of responsiveness thereto.

Figure 12A:
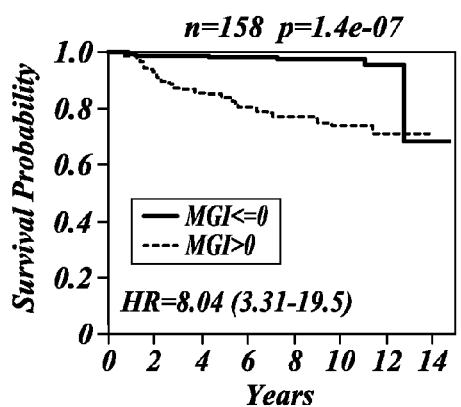
FIGS. 12A-12B show Kaplan-Meier curve analyses of patient stratification by MGI according to pre- or post-menopause status.
Figure 12B:
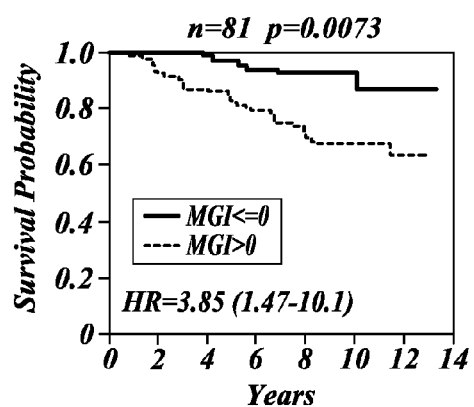

The disclosure further includes a method of determining MGI alone, H:I alone, or a combination of MGI and H:I determinations as a prognostic factor or predictor of clinical responsiveness in pre-menopausal women and post-menopausal women. FIG. 12 shows the ability of a "high risk" MGI to stratify both classes of women based upon survival outcomes. Post-menopausal women may be defined as those that are ≥50 years old while pre-menopausal women may be defined as those who are less than 50 years old. In both groups, "high risk" MGI is an indicator of increased likelihood of cancer recurrence over time relative to a "low risk" MGI. Of course the disclosure further includes a method of not selecting appropriate therapies for pre- and post-menopausal women based upon the MGI value, H:I value, or combination of both values determined from a sample from the woman.

More generally, a method to determine therapeutic treatment for a cancer patient may begin with assaying for MGI as described herein. The determined value may be used to classify the cancer as corresponding to a Grade I or Grade III tumor, or identify the subject as having a prognosis of likely cancer recurrence, or having responsiveness or non-responsiveness to therapies as described herein. The method may then include selecting treatment for a patient with such a tumor or such a prognosis or such responsiveness or non-responsiveness. In some cases, the selected treatment may include surgery and chemotherapy and/or radiation because the prognosis is poor and/or non-responsiveness to other therapies is indicated.

Further embodiments of the disclosure include a method of determining tumor grade or cancer risk in a subject diagnosed with benign cancer. The method may include assaying a sample of breast cells from the subject for the expression levels of Bub1B, CENPA, NEK2, RACGAP1, and RRM2, wherein said expression levels are correlated with a Grade I or Grade III tumor or a "high risk" or "low risk" of cancer. Embodiments of this method include determining the MGI value based on the expression levels, and optionally using it to select therapeutic treatment for the subject.

In other embodiments, the disclosure includes a method of determining tumor grade, or risk of local cancer recurrence, in a subject diagnosed with DCIS. The method may include assaying a sample of breast cancer cells from the subject for the expression levels of Bub1B, CENPA, NEK2, RACGAP1, and RRM2, wherein said expression levels are correlated with a Grade I or Grade III tumor or a "high risk" or "low risk" of local cancer recurrence.

While some of the above have been described in terms of using all five genes of the MGI in combination, the disclosure specifically includes use of fewer than five, including individual genes from among the five, in the practice of the disclosed methods. Additionally, the inclusion of other genes with one or more genes of the MGI or the H:I ratio in the foregoing is also expressly disclosed. Similarly, the use of H:I with substitution of another index, in whole or in part, for the MGI gene(s) is also expressly disclosed.

Therefore, the five genes of the MGI may be used singly with significant accuracy or in combination to increase the ability to accurately correlating a molecular expression phenotype with a tumor grade and/or cancer outcome. This correlation is a way to molecularly provide for the determination of cancer recurrence and/or survival outcomes as disclosed herein. Additional uses of the correlated genes are in the classification of cells and tissues; determination of diagnosis and/or prognosis; and determination and/or alteration of therapy.

The ability to discriminate is conferred by the identification of expression of the individual genes as relevant and not by the form of the assay used to determine the actual level of expression. An assay may utilize any identifying feature of an identified individual gene as disclosed herein as long as the assay reflects, quantitatively or qualitatively, expression of the gene in the "transcriptome" (the transcribed fraction of genes in a genome) or the "proteome" (the translated fraction of expressed genes in a genome). Identifying features include, but are not limited to, unique nucleic acid sequences used to encode (DNA), or express (RNA), said gene or epitopes specific to, or activities of, a protein encoded by said gene. All that is required is the identity of the gene(s) necessary to discriminate between cancer outcomes and an appropriate cell containing sample for use in an expression assay.

Similarly, the nature of the cell containing sample is not limiting, as fresh tissue, freshly frozen tissue, and fixed tissue, such as formalin-fixed paraffin-embedded (FFPE) tissues, may be used in the disclosed methods.

In one embodiment, the disclosure provides for the identification of the gene expression patterns by analyzing global, or near global, gene expression from single cells or homogenous cell populations which have been dissected away from, or otherwise isolated or purified from, contaminating cells beyond that possible by a simple biopsy. Because the expression of numerous genes fluctuate between cells from different patients as well as between cells from the same patient sample, the levels of gene expression may be determined in correspondence to one or more "control" or "normalization" genes, the expression(s) of which are relatively constant in the cells of a patient or between patients.

In another aspect, the disclosure includes physical and methodological means for detecting the expression of gene(s) identified by the models generated by individual expression patterns. These means may be directed to assaying one or more aspect of the DNA template(s) underlying the expression of the gene(s), of the RNA used as an intermediate to express the gene(s), or of the proteinaceous product expressed by the gene(s).

One advantage provided by the disclosure is that contaminating, non-cancer cells (such as infiltrating lymphocytes or other immune system cells) are not present to possibly affect the genes identified or the subsequent analysis of gene expression to identify the cancer recurrence and/or survival outcomes of patients. Such contamination is present where a biopsy containing many cell types is used to assay gene expression profiles.

While the present disclosure is described mainly in the context of human cancer, such as breast cancer, it may be practiced in the context of cancer of any animal. Preferred animals for the application of the present disclosure are mammals, particularly those important to agricultural applications (such as, but not limited to, cattle, sheep, horses, and other "farm animals"), animal models of cancer, and animals for human companionship (such as, but not limited to, dogs and cats).

The methods provided by the disclosure may also be automated in whole or in part.

Kits

The materials for use in the methods of the present disclosure are ideally suited for preparation of kits produced in accordance with well known procedures. The disclosure thus provides kits comprising agents for the detection of expression of the disclosed genes for grading tumors or determining cancer outcomes. Such kits optionally comprise the agent with an identifying description or label or instructions relating to their use in the methods of the present disclosure. Such a kit may comprise containers, each with one or more of the various reagents (typically in concentrated form) utilized in the methods, including, for example, pre-fabricated microarrays, buffers, the appropriate nucleotide triphosphates (e.g., dATP, dCTP, dGTP and dTTP; or rATP, rCTP, rGTP and UTP), reverse transcriptase, DNA polymerase, RNA polymerase, and one or more primer complexes of the present disclosure (e.g., appropriate length poly(T) or random primers linked to a promoter reactive with the RNA polymerase). A set of instructions will also typically be included.

Having now generally provided the disclosure, the same will be more readily understood through reference to the following examples which are provided by way of illustration, and are not intended to be limiting of the disclosure, unless specified.

EXAMPLES

Example I

General

Patients and Tumor Samples

Two public and previously published microarray datasets (accessions GSE3494, GSE1456) were downloaded from Gene Expression Omnibus (GEO, http://ncbi.nih.gov/geo). GSE3494 (Uppsala cohort) consists of 251 patients derived from a population-based cohort treated in Uppsala County, Sweden, from 1987 to 1989, and they were heterogeneous in terms of adjuvant systemic therapy received (untreated or endocrine and/or chemotherapy-treated). See Miller et al., *Proc. Natl. Acad. Sci. USA*, 102:13550-5 (2005). Clinical outcome data (breast cancer-specific death) were available for 236 patients with a median follow-up of 10 years. GSE1456 (Stockholm cohort) consists of a similar series of 159 breast cancer patients treated at the Karolinska Hospital, Stockholm, Sweden from 1994 to 199614. Both GSE3494 and GSE1456 contain gene expression data from frozen tumor samples analyzed on the Affymetrix U133A and U133B arrays (Affymetrix, Santa Clara, Calif.).

A second cohort of 239 patients used a retrospective case-cohort design (Pawitan et al., *Breast Cancer Res.*, 7:R953-64 (2005)) and was derived from 683 stage I to stage III patients with estrogen receptor-positive breast cancer treated at the Massachusetts General Hospital from 1991 to 1999. Clinical follow-up data were obtained from tumor registry and hospital records. Cases were all patients who developed distant metastasis during follow-up; controls were randomly selected from patients who remained disease-free at last follow-up to achieve a 2:1 ratio of controls to cases. In addition, controls were frequency-matched to cases with respect to adjuvant therapy and time of diagnosis. For about 80% of the cases and controls, both clinical outcome data and formalin-fixed paraffin-embedded (FFPE) tumor blocks were retrieved successfully.

The final cohort consisted of 79 cases and 160 controls, and its patient and tumor characteristics were summarized in Table 1. This study was approved by local Institutional Review Boards. This last cohort consisted of 84 of the Oxford series described previously (Loi et al., *J. Clin. Oncol.*, 25:1239-46 (2007)). All patients had estrogen receptor-positive breast cancer and were lymph node-negative and treated with tamoxifen adjuvant monotherapy. This study used portions of the total RNA from previously isolated frozen tumor samples.

TABLE 1

Patient and tumor characteristics

| Characteristics | Case (n = 79) | Controls (n = 160) |
|---|---|---|
| Relapse time (Years) | | |
| Mean | 4.6 | 9.1 |
| Range | 0.6-12.9 | 0.1-14.8 |
| Matched variables | | |
| Treatment | | |
| chemo | 11 (14%) | 9 (6%) |
| chemo + endo | 32 (41%) | 58 (36%) |
| endo | 28 (35%) | 67 (42%) |
| none | 8 (10%) | 26 (16%) |
| Year of Diagnosis | | |
| 1991-1995 | 40 (51%) | 74 (46%) |
| 1996-2000 | 39 (49%) | 86 (54%) |
| Unmatched variables | | |
| Age at diagnosis (years) | | |
| <35 | 11 (14%) | 5 (3%) |
| 35-44 | 14 (18%) | 22 (14%) |
| 45-49 | 11 (14%) | 18 (11%) |
| 50-59 | 12 (15%) | 55 (34%) |
| >=60 | 31 (39%) | 60 (38%) |
| Tumor size (cm) | | |
| <=1 | 7 (9%) | 34 (21%) |
| 1.1-2 | 32 (41%) | 65 (41%) |
| 2.1-4 | 33 (42%) | 46 (29%) |
| >4 | 7 (9%) | 15 (9%) |
| Tumor grade | | |
| 1 | 4 (5%) | 32 (20%) |
| 2 | 41 (52%) | 109 (68%) |
| 3 | 34 (43%) | 19 (12%) |
| Lymph node status | | |
| Neg | 37 (47%) | 97 (61%) |
| Pos | 39 (49%) | 52 (32%) |
| Unknown | 3 (4%) | 11 (7%) |
| Progesterone receptor | | |
| Neg | 19 (24%) | 20 (12%) |
| Pos | 60 (76%) | 140 (88%) |

Real-Time RT-PCR Assays for H/I and MGI

Primer and probe sequences for HOXB13 and IL17BR, as well as control genes ESR1, PGR, CHDH, ACTB, HMBS, SDHA and UBC, were used as described previously (Ma et al., supra). Primer and probe sequences for the five molecular grade genes (BUB1B, CENPA, NEK2, RACGAP1 and RRM2) as well as ERBB2 (HER2) were prepared using Primer Express (ABI).

For each FFPE sample, two 7-µm tissue sections were used for RNA extraction. Gross macro-dissection was used to enrich for tumor content. RNA extraction, reverse transcription, and TaqMan RT-PCR using the ABI 7900HT instrument (Applied Biosystem, Inc) were performed as described before (Ma et al., id.). The cycling threshold numbers (CTs) were normalized to the mean CT of four reference genes (ACTB, HMBS, SDHA and UBC). The use of these genes is supported by the previous reports regarding these genes and representative sequences of each of these genes known to the skilled person. Normalized CTs were taken to represent relative gene expression levels.

Calculation of H/I, MGI, and GGI

Generally, and with respect to MGI, it is preferred that the expression levels of the disclosed genes are combined to form a single index that serves as a strong prognostic factor and predictor of clinical outcome(s). The index is a summation of the expression levels of the genes used and uses coefficients determined from principle component analysis to combine cases of more than one disclosed gene into a single index. The coefficients are determined by factors such as the standard deviation of each gene's expression levels across a representative dataset, and the expression value for each gene in each sample. The representative dataset is quality controlled based upon the average expression values for reference gene(s) as disclosed herein.

Stated differently, and with respect to MGI, normalized expression levels for the five genes from microarrays or RT-PCR were standardized to mean of 0 and standard deviation of 1 across samples within each dataset and then combined into a single index per sample via principle component analysis (PCA) using the first principle component. Standardization of the primary expression data within each dataset was necessary to account for the different platforms (microarrays and RT-PCR) and sample types (frozen and FFPE). As a result, and following scaling parameters, a formula for the summation of expression values that defines the index is generated. The precision of the scaling parameters can then be tested based on the means, standard errors, and standard deviations (with confidence intervals) of the expression levels of the genes across the data set. Therefore, generation of the formula for the index is dependent upon the dataset, reference gene, and genes of the MGI.

The HOXB13:IL17BR ratio was calculated as the difference in standardized expression levels between HOXB13 and IL17BR as described previously (Ma et al., id.). The means and standard deviations for HOXB13 and IL17BR used for standardizing the Table 1 cohort were derived from an analysis of 190 FFPE tissue sections from a separate population-based cohort of estrogen receptor-positive lymph node-negative breast cancer patients.

For MGI, obviously abnormal raw $C_T$ values were removed prior to averaging the values over duplicates for each gene and each sample. The averaged raw $C_T$ value for each gene was then normalized by the averaged $C_T$ value of four reference genes (ACTB, HMBS, SDHA, and UBC). The normalized expression levels ($\Delta C_T$) for the five genes were combined into a single index per sample, which can be compared to a pre-determined cutoff value, such as 0, where high MGI is above the cutoff and low MGI is below the cutoff.

Genomic Grade Index (GGI) was calculated from microarray data using the 128 Affymetrix probe sets representing 97 genes and scaled within each dataset to have a mean of −1 for grade 1 tumors and +1 for grade 3 tumors as described previously (Sotiriou et al., supra).

Cut-Points and Statistical Analyses

H/I CUT-POINT: The cutpoint of 0.06 for the HOXB13: IL17BR ratio, previously defined to stratify patients treated with adjuvant tamoxifen into low and high risk of recurrence, was applied directly in this study.

MGI CUT-POINT: The calculation and the cutpoint for MGI were defined without using any clinical outcome data and instead was a natural cutpoint. Initial analysis of MGI in the Uppsala cohort indicated good discrimination of grade 1 and grade 3 tumors using the mean (0) as cutpoint, and model-based clustering of MGI also indicated a bimodal distribution with a natural cutpoint around 0. This cutpoint was further supported by receiver operating characteristic (ROC) analysis.

GENOMIC GRADE INDEX (GGI): GGI was dichotomized at the cutpoint of 0 as described previously (Sotiriou et al., supra).

STATISTICAL ANALYSES: Kaplan-Meier analysis with logrank test and Cox proportional hazards regression were performed to assess the association of gene expression indexes with clinical outcome. Multivariate Cox regression models were performed to assess the prognostic capacity of gene expression indexes after adjusting for known prognostic factors.

Proportional hazards (PH) assumption was checked by scaled Schoenfeld residuals; variables violating PH assumption were adjusted for in the model through stratification. To account for the case-cohort design of the Table 1 cohort, we used weighted Kaplan-Meier analysis and Cox regression models with modifications to handle case-cohort designs (see [19,20] as implemented in the survey package in R (www.r-project.org). To test for interaction between dichotomized MGI and the H:I ratio in Cox regression models, the Wald statistic was used in the Table 1 cohort and likelihood ratio test was used in the last cohort.

Correlations of continuous variables with categorical factors were examined using non-parametric two-sample Wilcoxon test or Kruskal-Wallis test for factors with more than two levels.

All statistical analyses were performed in the R statistical environment. All significance test were two-sided, and $p<0.05$ was considered significant.

Example II

Prognostic Performance of MGI in Breast Cancer Patients

The capacity of MGI to predict clinical outcome in breast cancer patients was examined using publicly available microarray datasets. MGI was first compared with the previously described 97-gene genomic grade index (GGI) in two independent datasets. ROC analysis indicated that MGI and GGI were comparable in discriminating grade 1 and grade 3 tumors (FIG. 2). In Kaplan-Meier analysis, MGI dichotomized at the cutpoint of 0 separated patients into two subgroups with significantly different risk of breast cancer death in both datasets, and the survival curves and hazard ratios (HR) were comparable to those generated by GGI (FIG. 2). These results thus demonstrated that a 5-gene index could reproduce the prognostic performance of the much more complex 97-gene signature. It is pointed out that even though MGI was developed entirely independently of GGI, four (BUB1B, CENPA, RACGAP1 and RRM2) of the five genes were among the 97-gene signature, and the fifth gene, NEK2, was just 2 positions down from the 112 grade 3-associated probe sets included in GGI.

Next, MGI was examined in a TRANSBIG study conducted to validate the Rotterdam 76-gene prognostic signature (Desmedt et al., Clin. Cancer Res., 13:3207-14 (2007)). This allowed the comparison of MGI to another validated prognostic signature in an unbiased manner. With the entire cohort, applying the cutpoint of 0 for MGI resulted in two patient groups with different risks of distant metastasis (HR=2.3, 95% CI 1.2-4.2, p=0.0064), whereas the risk stratification by the 76-gene signature was only marginally significant (p=0.046). See FIG. 3.

Furthermore, in the ER+ grade 1 or 2 subset (n=97), a group of patients for whom risk stratification is more challenging, MGI identified a subgroup of patients with significantly higher risk of recurrence (HR=3.3, 95% CI 1.3-8.4, p=0.0085), whereas the 76-gene signature did not (HR=1.4, p=0.57).

Taken together, in three large microarray datasets totaling 608 patients, MGI performed consistently as a strong prognostic factor comparable to or exceeding much more complex signatures.

Example III

Development and Validation of an RT-PCR Assay for MGI

Primers and probes for the 5 MGI genes were designed for the TaqMan real-time PCR (RT-PCR) assay format (Table 2).

TABLE 2

Primer and probes sequences for molecular grade index genes

| Gene | Forward primer | TaqMan MGB Probe | Reverse rimer |
|---|---|---|---|
| BUB1B | GCCTCAGAGCA ATGGTTGTAT (SEQ ID NO: 1) | ACTGTATGT GCTGTAAT (SEQ ID NO: 2) | TAGTGCATCTAAA TGTGTCCTAAATT (SEQ ID NO: 3) |
| CENPA | GTGCTTGTCAA CGGATGTGTAG (SEQ ID NO: 4) | TCAGAAACT TAATTGGG (SEQ ID NO: 5) | CATCAAAGCTTACA GGTTTTCTATTCA (SEQ ID NO: 6) |
| NEK2 | CCCATGAGCC ATGCCTTTC (SEQ ID NO: 7) | AGTACACAT GATATTTCG (SEQ ID NO: 8) | GTTGCTGAAGAAC AGTAAAACCAATT (SEQ ID NO: 9) |
| RACGAP1 | GGCATCCCAACT AACAATAAAGAG (SEQ ID NO: 10) | TATAAGGGAA GATTGTCAAT (SEQ ID NO: 11) | ATGACTGTAGCTT TTCTTACCACAAA (SEQ ID NO: 12) |
| RRM2 | CCTTTAACCAG CACAGCCAGTT (SEQ ID NO: 13) | AAAGATGC AGCCTCA (SEQ ID NO: 14) | CATTAAAATCT GCGTTGAAGCA (SEQ ID NO: 15) |

Compared to microarray-based platforms, real time RT-PCR offers higher precision in quantitation, especially in analyzing partially degraded RNA samples from formalin-fixed paraffin-embedded (FFPE) specimens (Cronin et al., Am. J. Pathol., 164:35-42 (2004)), which are the most common sample type in the clinical setting.

To validate the RT-PCR-based MGI assay, a retrospective case-cohort study was conducted. The cases were patients who were treated at the Massachusetts General Hospital (Boston, Mass.) between 1991 and 1999 but developed distant metastasis during follow-up, and the controls were randomly selected from patients who entered into the clinic during the same period and were disease-free at last follow-up (see Table 1 above). Patients were treated with standard of care including no systemic therapy, hormonal therapy and chemotherapy. To determine the therapy-independent prognostic utility of MGI, the controls with cases with respect to systemic therapy.

Figure 4C:
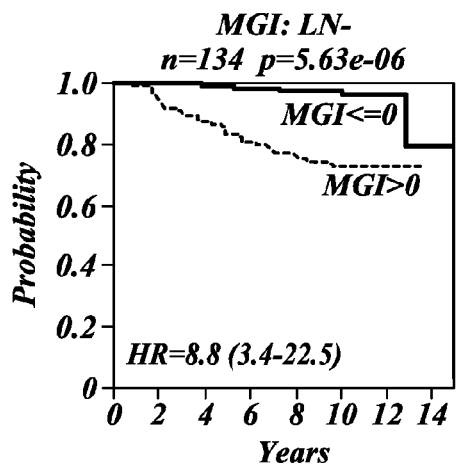
Figure 4D:
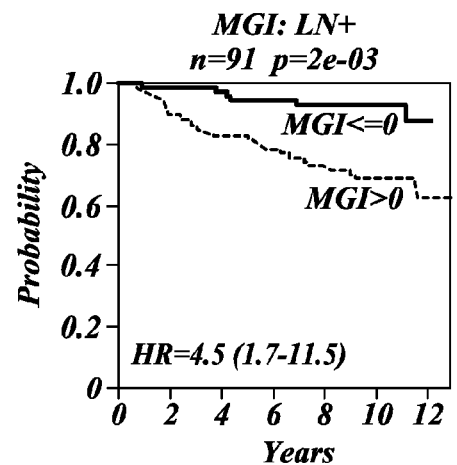

Similar to the microarray datasets analyzed above, the RT-PCR-based MGI also accurately discriminated grade 1 and grade 3 tumors (86% accuracy) using the same cutpoint of 0 as described before (FIG. 4A). Kaplan-Meier analysis indicated that high MGI was significantly associated with high risk of distant metastasis irrespective of nodal status (FIGS. 4B-D). In a multivariate Cox regression model adjusting for tumor size, tumor grade, lymph node status, systemic therapy, MGI remained highly significant with a hazard ratio of 4.7 (2.1-10.8) (Table 3).

TABLE 3

Multivariate Cox proportional hazards analysis of MGI in entire cohort

| Variable | | Hazard Ratio | 95% Confidence Interval | p |
|---|---|---|---|---|
| MGI | High vs. Low | 4.7 | 2.1-10.8 | 0.0002 |
| Tumor Size | >2 cm vs. <2 cm | 0.8 | 0.4-1.5 | 0.4580 |
| Tumor Grade | | | | 0.0011 |
| | II vs. I | 1.6 | 0.5-5.2 | 0.4331 |
| | III vs. I | 5.6 | 1.5-20.6 | 0.0105 |
| Age | >=35 yr vs. <35 yr | 0.7 | 0.2-1.9 | 0.4687 |
| Node Status | Pos. vs. Neg. | 1.2 | 0.6-2.3 | 0.5581 |
| Treatment | | | | 0.5733 |
| | Chemo vs. None | 0.9 | 0.4-2.4 | 0.8837 |
| | Endo vs. None | 1.5 | 0.5-4.5 | 0.4406 |
| | Chemo + Endo vs. None | 1.0 | 0.3-3.5 | 0.9939 |

Therefore, MGI as determined by RT-PCR maintained its high correlation with tumor grade and its robust prognostic performance in an entirely independent cohort.

Example IV

Complementary Prognostic Value of MGI and HOXB13:IL17BR

To demonstrate whether the HOXB13:IL17BR ratio provides additional prognostic information to MGI and vice versa, we analyzed both indexes in the lymph-node negative endocrine therapy-treated patients (n=93). The ratio has been shown not to be prognostic in lymph-node positive patients, which was confirmed in this cohort as well. In this patient group, MGI and the H:I ratio each was strongly associated with risk of distant metastasis (FIGS. 5A and B).

When both were considered together, MGI was highly significant in stratifying patients into low and high risk groups only when the tumors had high H:I, and likewise, the H:I ratio was only significant in stratifying patients with tumors having high MGI (FIG. 5E), although a formal test for interaction between these two indexes did not reach significance (p=0.09). Therefore MGI and the ratio were combined to stratify patients into three risk groups (low risk=low for both indexes or high for H:I only; intermediate risk=high for MGI only; and high risk=high for both, accounting for 48%, 24%, and 28% of the patients, respectively).

Kaplan-Meier analysis of these three groups indicated that high MGI and H:I together predicted very poor outcome for the high risk group (hazard ratio vs. low risk group=40.2, 95% CI 5.0-322.6). This is illustrated in FIG. 5C. The Kaplan-Meier estimates of 10-year distant metastasis-free survival probability were 98% (96-100%), 87% (77-99%) and 60% (47-78%) for the low, intermediate and high risk group, respectively. Furthermore, after adjusting for systemic therapy and standard prognostic factors (age, tumor size and grade) in a multivariate Cox regression model, the combined index remained highly statistically significant (Table 4), demonstrating the strong independent prognostic value of combining MGI and the H:I.

TABLE 4

Multivariate Cox proportional hazards model of combining MGI and HOXB13:IL17BR in node-negative patients treated with endocrine therapy or endocrine therapy + chemotherapy

| Variables | | Hazard Ratio | 95% Confidence Interval | P |
|---|---|---|---|---|
| MGI + HOXB13:IL17BR | | | | 0.0007 |
| | Intermediate vs. Low | 5.5 | 0.9-34.6 | 0.0720 |
| | High vs. Low | 24.2 | 4.3-135.2 | 0.0003 |
| Tumor Size | >2 cm vs. <=2 cm | 1.0 | 0.3-2.9 | 0.9804 |
| Age | >=35 yr vs. <35 yr | 0.1 | 0.0-0.4 | 0.0036 |
| Treatment | Endo vs Chemo + Endo | 11.5 | 2.2-59.4 | 0.0034 |

Note:
Tumor grade was adjusted for by stratification.

To further substantiate the prognostic power of combining MGI and the H:I ratio, we examined these two indexes in another independent cohort of 84 ER+ lymph node-negative patients uniformly treated with adjuvant tamoxifen therapy (last cohort). After applying the same cutpoints to these two indexes and the same combination algorithm as described above, the resulting low, intermediate and high risk groups consisted of 44%, 24% and 32% of the patients, respectively, in keeping with their proportions seen in the Table 1 cohort. Again, Kaplan-Meier analysis indicated that the high risk group with tumors high for both indexes had the worst clinical outcome (HR vs. low risk group=7.9 (2.2-28.2) (FIG. 5D), and likelihood ratio test indicated a statistically significant interaction between these two indexes (p=0.036).

Taken together, in two independent cohorts, MGI and the H:I ratio provided additional prognostic information to each other, and combining both indexes was particularly effective in identifying a subset of patients (~30%) with very poor outcome despite endocrine therapy, indicating a need of additional therapies for these patients.

Example V

Differential Correlation of HOXB13:IL17BR and MGI with ER and PR Expression

Figure 6:
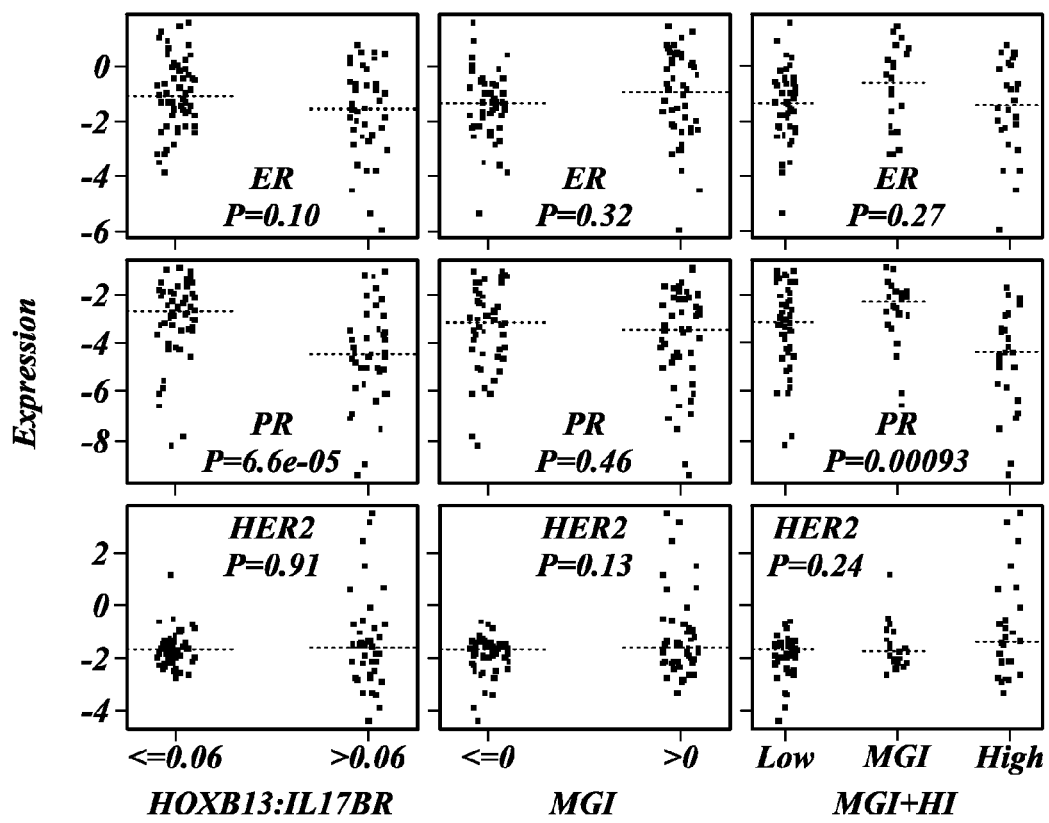
FIG. 6 shows correlation of the H:I ratio and MGI with ER, PR and HER2 expression as determined by real-time RT-PCR in the lymph node-negative endocrine therapy-treated patients of the Table 1 cohort. X-axis, groups defined by the H:I ratio, MGI or their combination. Y-axis, relative expression level of ER, PR or HER2 as indicated.
Figure 7:
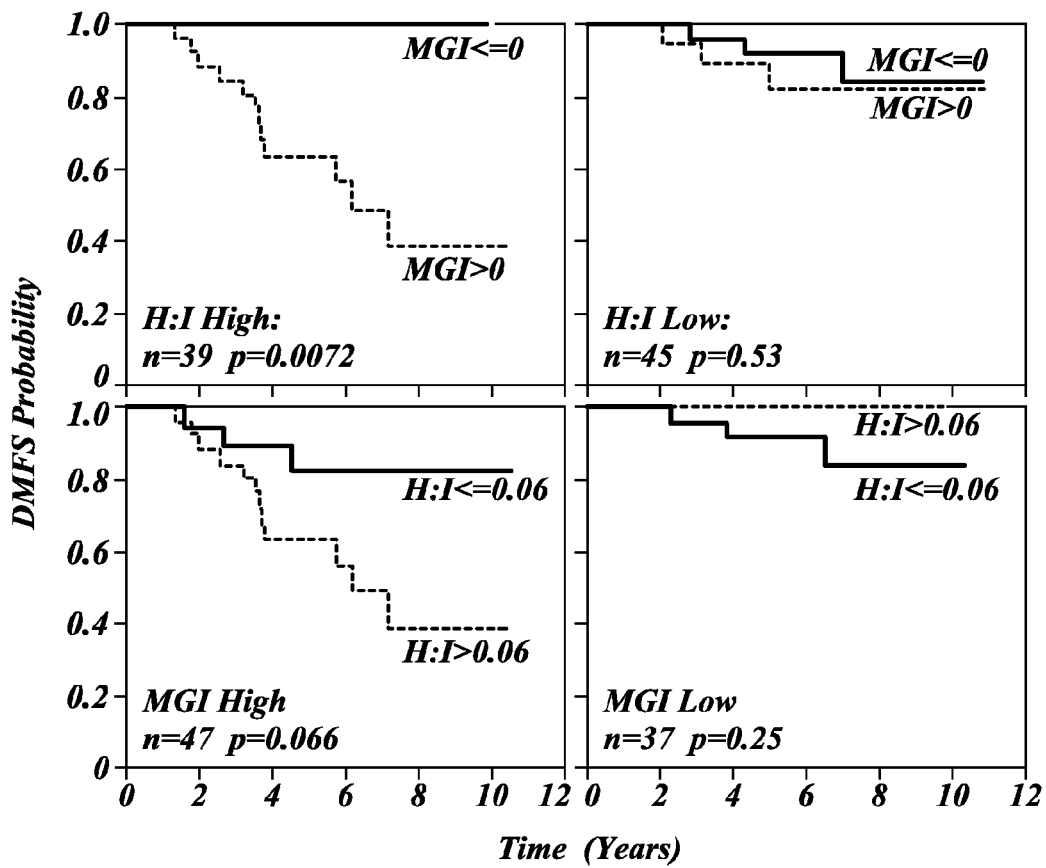
FIG. 7 illustrates the interaction between MGI and the H to I ratio in the last cohort. Similar to the Table 1 cohort, MGI and the H:I ratio provide additional prognostic information to each other. Tumors with high values in both indexes were associated with much worse outcome than those with only one high index.

HOXB13 and IL17BR are both regulated by estrogen receptor. HOXB13 expression is suppressed while IL17BR expression is stimulated by estrogen in ER+ breast cancer cell lines (Zuncai et al., *Clin. Cancer Res.*, (2007)). So the expression of the 5-genes in MGI was tested for possible similar regulation by estrogen signaling. In the ER+ node-negative endocrine-treated patient group analyzed above, where high H:I was strongly correlated with lower PR expression, MGI was not significantly associated with either ER or PR mRNA expression (FIG. 6).

In the three risk groups generated by combining the H:I ratio and MGI as described above, the high risk group was associated with poor PR expression. Interestingly, the high risk group was also particularly enriched for HER2 overexpressing tumors (FIG. 6). It contained 6 of the 7 tumors with high HER2 expression (using 0 as cutoff, Fisher's exact test p=0.001). Therefore, the high risk group had tumors with both decreased PR and increased HER2 expression, both markers of endocrine resistance (Shou et al., *J. Natl. Cancer Inst.*, 96:926-35, (2004)). This is consistent with its poor outcome despite endocrine therapy. These results also suggest that the H:I ratio and MGI likely represent distinct biological pathways, which may explain their usefulness in determining tumor aggressiveness when used together.

Example VI

MGI is Significantly Associated with pCR

Tumor samples from 82 ER+ patients treated pre-operatively with paclitaxel followed by 5-FU, doxorubicin and cyclophosphamide (paclitaxel/FAC), a commonly used therapy for breast cancer, were used to study MGI correlation to sensitivity to chemotherapy. 7 of 82 (8.5%) ER+ patients had a complete pathological response (pCR) and all 7 patients had a high MGI. No tumors with a low MGI (~55%) had a pCR in the corresponding patient. See FIG. 9. Approximately 20% of high MGI tumors had a pCR, or an enrichment of 2.3 fold and a 100% positive predictive value.

So high MGI is significantly associated with a pathological complete response (pCR) in ER+ tumors (p=0.0053). And MGI indicates which tumors will have a likelihood to be either sensitive or resistant to chemotherapy. The results demonstrate that MGI and Oncotype DX have similar performance in predicting chemo-response in pre-operative setting (Chang et al., *Breast Cancer Research and Treatment*, 10.1007/s10549-007-9590 (2007)).

BIBLIOGRAPHY

1. Ma et al., *Cancer Cell*, 5:607-16 (2004)
2. Ma et al., *J. Clin. Oncol.*, 24:4611-9 (2006)
3. Goetz et al., *Clin. Cancer Res.*, 12:2080-7 (2006)
4. Jerevall et al., *Breast Cancer Res. Treat* (2007)
5. Jansen et al., *J. Clin. Oncol.* 25:662-8 (2007)
6. Cianfrocca et al., *Oncologist*, 9:606-16 (2004)
7. Sotiriou et al., *J. Natl. Cancer Inst.*, 98:262-72 (2006)
8. van 't Veer et al., *Nature*, 415:530-6 (2002)
9. Paik et al., *N. Engl. J. Med.*, 351:2817-26 (2004)
10. Desmedt et al., *Cell Cycle*, 5:2198-202 (2006)
11. Loi et al. *J. Clin. Oncol.*, 25:1239-46 (2007)
12. Sotiriou et al., *Nat. Rev. Cancer*, 7:545-53 (2007)
13. Miller et al., *Proc. Natl. Acad. Sci. USA*, 102:13550-5 (2005)
14. Pawitan et al., *Breast Cancer Res.* 7:R953-64 (2005)
15. Rundle et al., *Cancer Epidemiol Biomarkers Prev.*, 14:1899-907 (2005)
16. Ma et al., *Proc. Natl. Acad. Sci. USA*, 100:5974-9 (2003)
17. Whitfield et al., *Mol. Biol. Cell*, 13:1977-2000 (2002)
18. Hirose et al., *J. Biol. Chem.*, 276:5821-5828 (2001)
19. Goldhirsch et al., *Ann. Oncol.*, 16:1569-83 (2005)

All references cited herein, including patents, patent applications, and publications, are hereby incorporated by reference in their entireties, whether previously specifically incorporated or not.

Having now fully described the inventive subject matter, it will be appreciated by those skilled in the art that the same can be performed within a wide range of equivalent parameters, concentrations, and conditions without departing from the spirit and scope of the disclosure and without undue experimentation.

While this disclosure has been described in connection with specific embodiments thereof, it will be understood that it is capable of further modifications. This application is intended to cover any variations, uses, or adaptations of the disclosure following, in general, the principles of the disclosure and including such departures from the present disclosure as come within known or customary practice within the art to which the disclosure pertains and as may be applied to the essential features hereinbefore set forth.

What is claimed is:

1. A method of predicting responsiveness of a breast cancer afflicted subject to chemotherapy, the method comprising:

obtaining a sample of breast cancer cells from the subject;

assaying a sample of breast cancer cells from the subject for mRNA expression levels of fewer than 97 genes, including Bub1B and at least one of NEK2, RACGAPI, and RRM2, by producing cDNA from mRNA of the fewer than 97 genes and detecting the cDNA to determine normalized expression levels of the fewer than 97 genes;

combining the normalized expression levels as a single index into a subject's index using coefficients determined from principle component analysis;

comparing the subject's index with an index from data from breast cancer tissue in a representative dataset comprising normalized expression levels of fewer than 97 genes, including Bub1B and at least one of NEK2, RACGAPI, and RRM2 from patients that were responsive to chemotherapy and breast cancer patients that were not responsive to chemotherapy; and wherein the cancer of the subject is not likely to be responsive if the subject's index is below a predetermined cutoff value determined from the index from data of breast cancer tissue from the representative dataset, and the cancer of the subject is likely to be responsive if the subject's index is above the predetermined cutoff value; and treating the subject with paclitaxel followed by 5-fluorouracil, doxorubicin and cyclophosphamide (paclitaxel/FAC), taxol or anthracyclin therapy if the method predicts responsiveness, and treating the subject with surgery or radiation if the method does not predict responsiveness.

2. The method of claim 1, wherein expression levels of all of Bub1B, CENPA, NEK2, RACGAPI, and RRM2 are assayed.

3. The method of claim 2, further comprising assaying for the H:I ratio in said sample.

4. A method of determining whether a breast cancer afflicted subject has a Grade I tumor or a Grade III tumor, or has an increased risk of cancer recurrence, the method comprising:

obtaining a sample of breast cancer cells from the subject;

assaying a sample of breast cancer cells from the subject for mRNA the expression levels of fewer than 97 genes, including Bub1B and at least one of NEK2, RACGAPI, and RRM2, by producing cDNA from mRNA of the fewer than 97 genes and detecting the cDNA to determine normalized expression levels of the fewer than 97 genes; and combining the normalized expression levels as a single index into a subject's index using coefficients determined from principle component analysis;

comparing the subject's index with a predetermined cutoff value determined from data comprising expression levels of fewer than 97 genes, including Bub1B and at least one of NEK2, RACGAPI, and RRM2 from breast cancer tissue in a representative dataset from patients that (a) had a Grade I tumor or (b) that had a Grade III tumor, or had cancer recurrence; and determining whether the subject has a Grade I tumor or a Grade III tumor, or has an increased risk of cancer recurrence, wherein the cancer of the subject is likely to be Grade I, or the subject is unlikely to have cancer recurrence, if the subject's index is below the predetermined cutoff value, and the cancer of the subject is likely to be Grade III, or the subject is likely to have32) cancer recurrence, if the subject's index is above the predetermined cutoff value; and treating the subject with surgery, chemotherapy or radiation if the method determines that the subject has a grade III tumor, and treating the subject with surgery or endocrine therapy if the method determines that the subject has a grade I tumor.

5. The method of claim 4 further comprising assaying for the HoxB13:IL17BR (H:I) ratio in said sample.

6. The method of claim 4 wherein said cancer is ductal carcinoma in situ (DCIS) and said cancer recurrence comprises local recurrence.

7. The method of claim 4, wherein expression levels of all of Bub Bub1B, CENPA, NEK2, RACGAPI, and RRM2 are assayed.

8. The method of claim 7, further comprising assaying for the H:I ratio in said sample.

9. The method of claim 4, wherein the expression levels of fewer than 21 genes are assayed.

* * * * *

UNITED STATES PATENT AND TRADEMARK OFFICE
CERTIFICATE OF CORRECTION

PATENT NO. : 9,447,470 B2
APPLICATION NO. : 12/718973
DATED : September 20, 2016
INVENTOR(S) : Mark G. Erlander, Xiao-Jun Ma and Dennis C. Sgroi It is certified that error appears in the above-identified patent and that said Letters Patent is hereby corrected as shown below:

In the Claims

Column 61, Line 44, Claim 1 delete the term "RACGAPI" and replace it with --RACGAP1--.

Column 61, Line 60, Claim 2 delete the term "RACGAPI" and replace it with --RACGAP1--.

Column 61, Line 63, Claim 3 delete the term "H:I" and replace it with --HoxB13:IL17BR (H:I)--.

Column 62, Line 27, Claim 4 delete the phrase "mRNA the expression levels" and replace it with --mRNA expression levels--.

Column 62, Line 28, Claim 4 delete the term "RACGAPI" and replace it with --RACGAP1--.

Column 62, Line 53, Claim 4 delete the term "have32)" and replace it with --have--.

Column 62, Line 66, Claim 7 delete the term "Bub Bub1B" and replace it with --Bub1B--.

Column 62, Line 66, Claim 7 delete the term "RACGAPI" and replace it with --RACGAP1--.

Signed and Sealed this
Twelfth Day of December, 2017

Joseph Matal
*Performing the Functions and Duties of the*
*Under Secretary of Commerce for Intellectual Property and*
*Director of the United States Patent and Trademark Office*